(12) United States Patent
Hu et al.

(10) Patent No.: US 9,861,613 B2
(45) Date of Patent: Jan. 9, 2018

(54) GPR142 AGONIST COMPOUNDS

(71) Applicant: Eli Lilly and Company, Indianapolis, IN (US)

(72) Inventors: Zhi Long Hu, Shanghai (CN); Lian Zhu Liu, Shanghai (CN); Tianwei Ma, Shanghai (CN); Mi Emily Zeng, Shanghai (CN); Jingye Zhou, Shanghai (CN)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/116,230

(22) PCT Filed: Jan. 22, 2015

(86) PCT No.: PCT/CN2015/071286
§ 371 (c)(1),
(2) Date: Aug. 3, 2016

(87) PCT Pub. No.: WO2015/120768
PCT Pub. Date: Aug. 20, 2015

(65) Prior Publication Data
US 2017/0165234 A1    Jun. 15, 2017

(30) Foreign Application Priority Data
Feb. 14, 2014 (WO) ................ PCT/CN2014/072083

(51) Int. Cl.
| A61K 31/4164 | (2006.01) |
|---|---|
| A61K 31/4178 | (2006.01) |
| A61K 31/4174 | (2006.01) |
| A61K 31/5375 | (2006.01) |

(52) U.S. Cl.
CPC ...... *A61K 31/4174* (2013.01); *A61K 31/4178* (2013.01); *A61K 31/5375* (2013.01); *A61K 2121/00* (2013.01)

(58) Field of Classification Search
CPC .................. A61K 31/4164; A61K 31/4178
See application file for complete search history.

(56) References Cited

U.S. PATENT DOCUMENTS

| 7,754,717 B2 | 7/2010 | Dimauro et al. |
|---|---|---|
| 8,188,098 B2 | 5/2012 | Erickson et al. |

OTHER PUBLICATIONS

Mike Lizarzaburu et al. "Discovery and Optimization of a Novel Series of GPR142 Agonists for the Treatment of Type 2 Diabetes Mellitus", Bioorganic & Medicinal Chemistry Letters, No. NO.22, Jul. 23, 2012 (Jul. 23, 2012), 5942-5947.

Narihiro Toda et al. "Potent and Orally Bioavailable GPR142 Agonists as Novel Insulin Secretagogues for the Treatment of Type 2 Diabetes", ACS Medicinal Chemistry Letters, No. NO. 4, Jun. 17, 2013 (Jun. 17, 2013), 790-794.

*Primary Examiner* — Rebecca L Anderson
(74) *Attorney, Agent, or Firm* — James B. Myers

(57) ABSTRACT

The present invention provides compounds of the Formula (Ia) wherein R is selected from the group consisting of $CH_3$, $CH(CH_3)_2$, $CH_2CN$, $CH_2CHF_2$, $CH_2CF_3$, (A), (B), (C), (D), (E), (F), $CH_2CH_2OCH_3$, and $CH_2C(O)OCH(CH_3)_2$; $R^1$ is selected from the group consisting of $CF_3$, $OCF_3$, and Cl; $R^2$ is selected from the group consisting of H and F; or a pharmaceutically acceptable salt thereof.

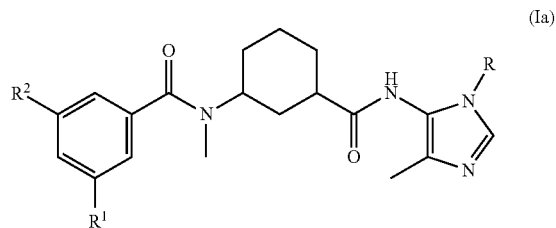

(Ia)

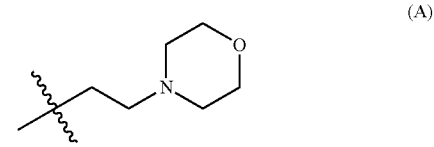

(A)

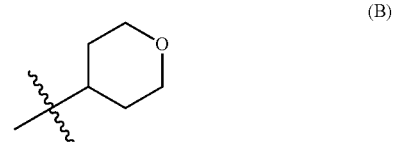

(B)

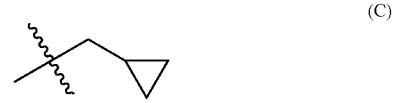

(C)

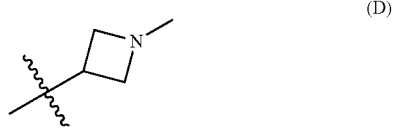

(D)

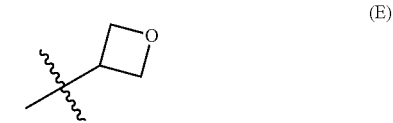

(E)

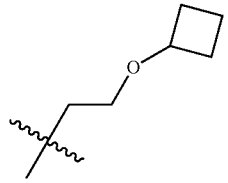

13 Claims, No Drawings

GPR142 AGONIST COMPOUNDS

This invention relates to imidazo benzamide compounds, or pharmaceutically acceptable salts thereof, and therapeutic use thereof. Compounds of this invention are GPR142 agonists.

GPR142 is reported to be expressed in pancreatic cells and associated with the stimulation of insulin secretion under conditions of high blood glucose. Compounds that effectuate GPR142 agonism are desired.

A series of phenylalanine based compounds for GPR142 agonism are disclosed in M. Lizarzaburu, et al. "Discovery and Optimization of a novel series of GPR142 agonists for the treatment of type 2 diabetes," Bioorganic and Medicinal Chemistry Letters 22 (2012) 5942-5947.

The present invention provides compounds with GPR142 agonist activity.

The present invention provides compounds of the Formula Ia below:

Ia

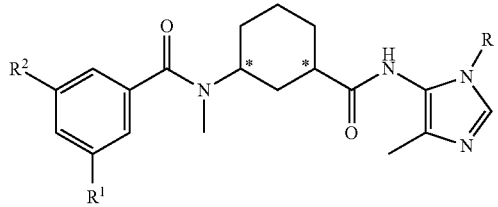

wherein R is selected from the group consisting of $CH_3$, $CH(CH_3)_2$, $CH_2CN$, $CH_2CHF_2$, $CH_2CF_3$,

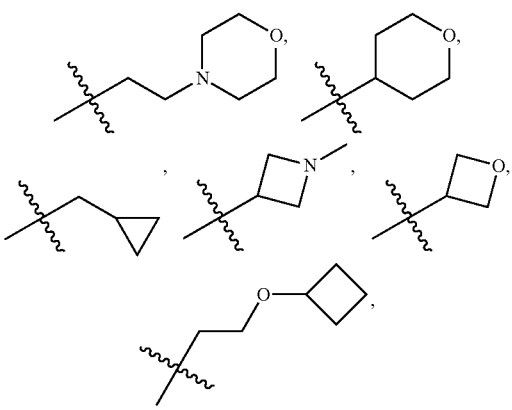

$CH_2CH_2OCH_3$, and $CH_2C(O)OCH(CH_3)_2$;

$R^1$ is selected from the group consisting of $CF_3$, $OCF_3$, and Cl;

$R^2$ is selected from the group consisting of H and F;

or a pharmaceutically acceptable salt thereof.

The invention further provides a compound of the Formula

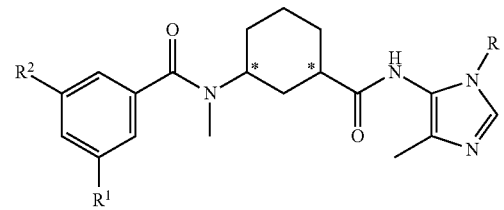

wherein R is selected from the group consisting of $CH(CH_3)_2$, $CH_2CN$, $CH_2CHF_2$, $CH_2CF_3$,

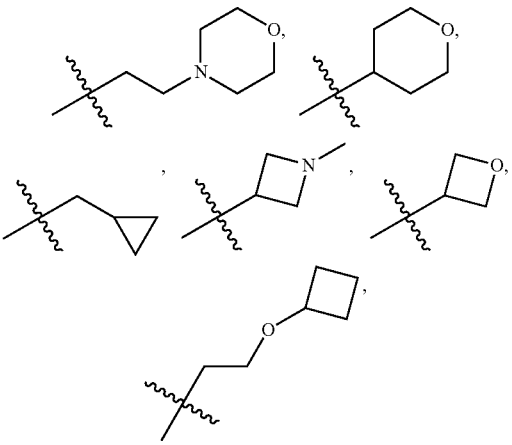

$CH_2CH_2OCH_3$, and $CH_2C(O)OCH(CH_3)_2$;

$R^1$ is selected from the group consisting of $CF_3$, $OCF_3$, and Cl;

$R^2$ is selected from the group consisting of H and F;

or a pharmaceutically acceptable salt thereof.

The present invention provides compounds of the Formula I below:

I

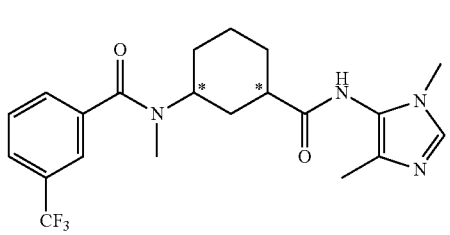

or a pharmaceutically acceptable salt thereof.

The compounds of the present invention have chiral carbons identified by the asterisks (*) in the structure above. The artisan will appreciate that the compounds of the invention exist as cis and trans isomers. Both cis and trans isomers are contemplated by the present invention. The cis configuration is preferred. The preferred isomer is isomer 1.

In an embodiment, $R^2$ is H; R is selected from the group consisting of $CH_3$, $CH(CH_3)_2$, $CH_2CN$, $CH_2CHF_2$, $CH_2CF_3$,

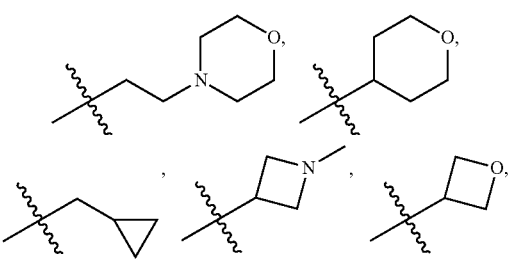

-continued

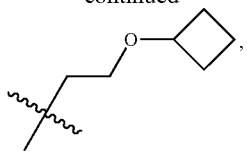

CH₂CH₂OCH₃, and CH₂C(O)OCH(CH₃)₂;

R¹ is selected from the group consisting of CF₃, OCF₃, and Cl; or a pharmaceutically acceptable salt thereof.

In an embodiment, R² is H; R¹ is CF₃; and R is selected from the group consisting of CH₃, CH(CH₃)₂, CH₂CN, CH₂CHF₂, CH₂CF₃,

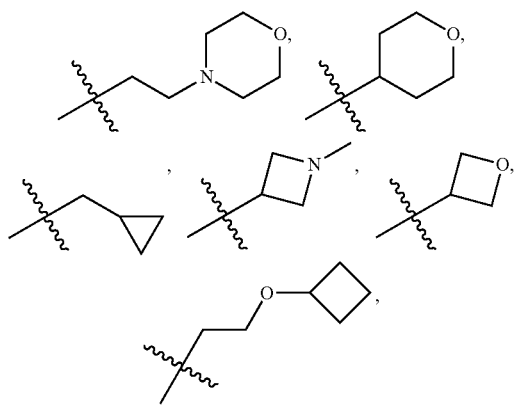

CH₂CH₂OCH₃, and CH₂C(O)OCH(CH₃)₂; or a pharmaceutically acceptable salt thereof. In an embodiment, R² is H; R¹ is CF₃; and R is selected from the group consisting of CH₃, CH(CH₃)₂, CH₂CN, CH₂CHF₂, CH₂CF₃, CH₂CH₂OCH₃, and CH₂C(O)OCH(CH₃)₂, or a pharmaceutically acceptable salt thereof. In an embodiment, R² is H; R¹ is CF₃; and R is selected from the group consisting of

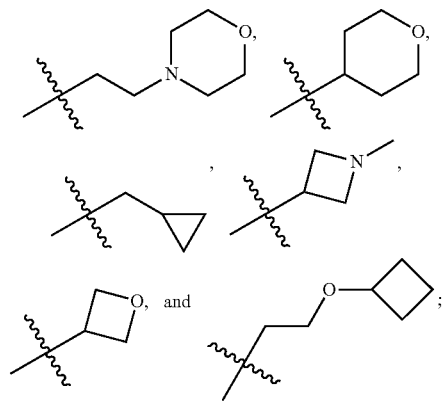

or a pharmaceutically acceptable salt thereof. In an embodiment, R² is H; R¹ is CF₃; and R is selected from the group consisting of CH₃, CH(CH₃)₂, CH₂CN, CH₂CHF₂, CH₂CF₃, CH₂CH₂OCH₃, and CH₂C(O)OCH(CH₃)₂; or a pharmaceutically acceptable salt thereof.

In an embodiment, R is selected from the group consisting of CH₃, CH(CH₃)₂, CH₂CN, CH₂CHF₂, CH₂CF₃,

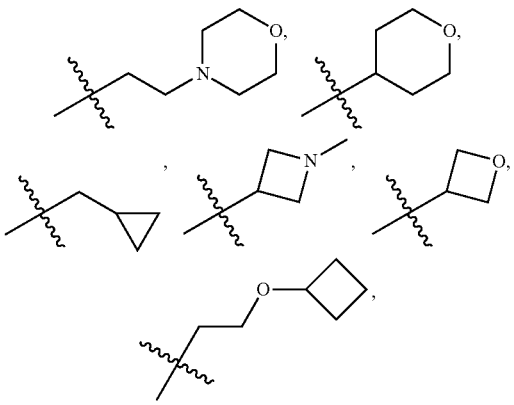

CH₂CH₂OCH₃, and CH₂C(O)OCH(CH₃)₂;

R¹ is OCF₃; R² is H; or a pharmaceutically acceptable salt thereof.

A preferred compound of the invention is Cis-(chiral)-N-[3-[(3,5-Dimethylimidazol-4-yl)carbamoyl]cyclohexyl]-N-methyl-3-(trifluoromethyl)benzamide or a pharmaceutically acceptable salt thereof.

The invention also provides a method for treating type II diabetes in a patient, comprising administering to a patient in need of such treatment an effective amount of a compound of Formula Ia, or a pharmaceutically acceptable salt thereof. The invention provides a method of augmenting insulin levels in a patient with type II diabetes, comprising administering to a patient in need of such treatment, an effective amount of a compound of Formula Ia, or a pharmaceutically acceptable salt thereof. The invention provides a method for treating a condition modulated by GPR142 agonism in a patient in need of such treatment, comprising administering an effective amount of a compound of Formula Ia, or a pharmaceutically acceptable salt thereof.

This invention provides a compound of Formula Ia, or a pharmaceutically acceptable salt thereof, for use in therapy, in particular for use in the treatment of type II diabetes or for use in the augmentation of insulin levels in a patient with type II diabetes. Even furthermore, this invention provides the use of a compound of Formula Ia, or a pharmaceutically acceptable salt thereof, for use in the manufacture of a medicament. This invention also provides the use of a compound of Formula Ia, or a pharmaceutically acceptable salt thereof, for use in the manufacture of a medicament for use in the treatment of type II diabetes. This invention provides the use of a compound of Formula Ia, or a pharmaceutically acceptable salt thereof, for use in the manufacture of a medicament for the augmentation of insulin levels in a patient with type II diabetes.

The invention further provides a pharmaceutical composition, comprising a compound of Formula Ia, or a pharmaceutically acceptable salt thereof, with one or more pharmaceutically acceptable carriers, diluents, or excipients. Provided in another embodiment of the invention, is a pharmaceutical composition comprising a compound of Formula Ia, or a pharmaceutically acceptable salt thereof, with one or more pharmaceutically acceptable carriers, diluents, or excipients. The invention provides a pharmaceutical composition, comprising a compound of Formula Ia, or a pharmaceutically acceptable salt thereof, with one or more pharmaceutically acceptable carriers, diluents, or excipients, and further comprising a second pharmaceutically active agent. The skilled artisan will recognize that the second pharmaceutically active agent is suitable for administration sequentially or concomitantly with a GPR142 agonist. A preferred second pharmaceutical agent is, for example, metformin.

The term "pharmaceutically-acceptable salt" refers to a salt of the compound of the invention considered to be acceptable for clinical and/or veterinary use. Pharmaceutically acceptable salts and common methodology for preparing them are well known in the art. See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

The term "treating" (or "treat" or "treatment") as used herein refers to restraining, slowing, or stopping the progression or severity of an existing symptom, condition, or disorder. It is preferred that "treating" includes augmenting insulin levels in a patient with type II diabetes.

Compounds of the present invention are GPR142 agonists, and may be useful for treating a disease or condition associated with a decrease in GPR142. Compounds of the present invention may be useful in the treatment of a disease or condition associated with the modulation of GPR142.

As used herein, "patient" refers to an animal in need of treatment, preferably not exclusively a mammal. A preferable embodiment is a patient that is a mammal, which is preferably a human. Another preferable embodiment is a patient that is a companion animal such as a dog, cat, or a fowl.

As used herein, the term "effective amount" refers to the amount or dose of compound of the invention or a pharmaceutically acceptable salt thereof which upon single or multiple dose administration to the patient, provides the desired effect in the patient. It will be understood that the amount of active agent actually administered will be determined by a physician, in light of the relevant circumstances, including the condition to be treated, the chosen route of administration, the actual active agent administered, the age, weight, and response of the individual patient, and the severity of the patient's symptoms and other relevant circumstances.

A compound of the present invention is preferably formulated as pharmaceutical compositions administered by any route which makes the compound bioavailable. Most preferably, such compositions are for oral administration. Such pharmaceutical compositions and processes for preparing same are well known in the art. See, e.g., *Remington: The Science and Practice of Pharmacy* (D. B. Troy, Editor, 21st Edition, Lippincott, Williams & Wilkins, 2006).

PREPARATIONS AND EXAMPLES

The following Preparations and Examples further illustrate the invention and represent a typical synthesis of the compound of the invention. It should be understood that the Preparations and Example are set forth by way of illustration and not limitation, and that various modifications may be made by one of ordinary skill in the art.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of Formula Ia, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. The reagents and starting materials are generally available to one of ordinary skill in the art. Others may be made by standard techniques of organic and heterocyclic chemistry, techniques which are known to one of ordinary skill in the art, and the procedures described in the Examples and Preparations which follow including any novel procedures.

Individual isomers, enantiomers, or diastereomers may be separated or resolved by one of ordinary skill in the art at any convenient point in the synthesis of a compound of Formula Ia by methods such as chiral chromatography or elective crystallization techniques (See for example, J. Jacques, et al., "Enantiomers, Racemates, and Resolutions", John Wiley and Sons, Inc., 1981, and E. L. Eliel and S. H. Wilen, "*Stereochemistry of Organic Compounds*", Wiley-Interscience, 1994). The designations "isomer 1" and "isomer 2" refer to the compounds that elute from chiral chromatography first and second, respectively, and if chiral chromatography is initiated early in the synthesis, the same designation is applied to subsequent intermediates and examples. The skilled artisan will recognize that the first eluting isomer may vary depending on the elution conditions.

Additionally, the intermediates described in the following Schemes and preparations may contain a number of nitrogen, hydroxy, or acid protecting groups. The variable protecting group may be the same or different in each occurrence depending on the particular reaction conditions and the particular transformations to be performed. The protection and deprotection conditions are well known to the skilled artisan and are described in the literature (See for example *Greene's Protective Groups in Organic Synthesis*, T. W. Greene and P. G. M. Wuts, eds., Fourth Edition, John Wiley and Sons, Inc., 2006).

The abbreviations used herein are defined according to *Aldrichimica Acta*, Vol. 17, No. 1, 1984. Other abbreviations are defined as follows: "BSA" refers to Bovine Serum Albumin; "CDI" refers to 1,1'-carbonyldiimidazole; "DCC" refers to 1,3-dicyclohexylcarbodiimide; "DIC" refers to 1,3-diisopropylcarbodiimide; "DMSO" refers to dimethylsulfoxide; "$EC_{50}$" refers to the effective concentration at half the maximal response; "ee" refers to enantiomeric excess; "Ex" refers to example; "FBS" refers to Fetal Bovine Serum; "HATU" refers to (dimethylamino)-N,N-dimethyl (3H-[1,2,3]triazolo[4,5-b]pyridin-3-yloxy)methaniminium hexafluorophosphate "HBSS" refers to Hank's Balanced Salt Solution; "HEK" refers to human embryonic kidney; "HEPES" refers to 4-(2-hydroxyethyl)-1-piperazineethanesulfonic acid; "HOAt" refers to 1-hydroxy-7-azobenzotriazole; "HOBt" refers to 1-hydroxylbenzotriazole hydrate; "HBTU" refers to refers to 2-(1H-benzotriazole-1-yl)-1,1,3,3-tetramethyluronium hexafluorophosphate; "HPLC" refers to High Performance Liquid Chromatography; "HTRF" refers to homogenous time resolved fluorescence; "IP-1" refers to inositol monophosphate; "KRB" refers to Krebs ringer buffer; "PG" refers to protecting group; "Prep" refers to preparation; "PyBOP" refers to benzotriazol-1-yloxytripyrrolidino-phosphonium hexafluorophosphate; "PyBrop" refers to bromo-tris-pyrrolidino phosphoniumhexafluoro phosphate; "RPMI" refers to Roswell Park Memorial Institute; "RT" refers to retention time; "SFC" refers to supercritical fluid chromatography; and "TFA" refers to trifluoroacetic acid.

Scheme 1

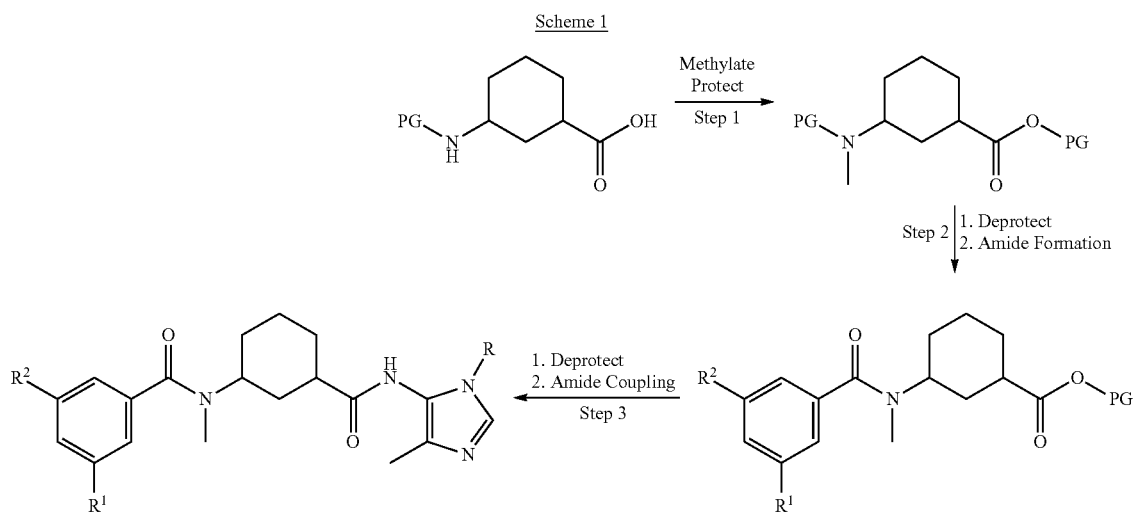

In Scheme 1, an amide coupling is accomplished with the amine of a 3-amino cyclohexanecarboxylic acid followed by an amide coupling on the carboxylic acid to give an-N-[3-[(3-substituted,5 methyl imidazol-4-yl)carbamoyl]cyclohexyl]-N-methyl-3,5 substituted benzamide. For example in Step 1, the protected amine can be methylated and the 3-carboxylic acid can be protected simultaneously under conditions well known in the art with a base such as sodium hydride at a temperature of about 0° C. using a methylating agent such as methyl iodide in a solvent such as dimethylformamide to give the product of Step 1. In substep 1 of Step 2, the amine can be deprotected under conditions well known in the art using an acid such as TFA at room temperature in a solvent such as dichloromethane. In substep 2 of Step 2, an acid chloride can be reacted with the amine using an organic base such as triethylamine in a solvent such as dichloromethane to give the amide product of Step 2. One skilled in the art can recognize that a carboxylic acid can be converted to the acid chloride using oxalyl chloride and a catalytic amount of dimethylformamide in a solvent such as dichloromethane. Alternatively, an amide coupling can be accomplished with an appropriate carboxylic acid and amine to give the product of Step 2. For example, the amide product of Step 2 can be reacted with a carboxylic acid using a coupling agent in a solvent such as pyridine, dimethformamide, or dichloromethane at room temperature or with heating. One skilled in the art will recognize that there are a number of methods and reagents for amide formation. For example, the reaction of the amine compound with an appropriate carboxylic acid in the presence of a coupling reagent with or without an organic base such as diisopropylethylamine or triethylamine can provide a compound of Step 2. Coupling reagents include carbodiimides, such as DCC, DIC, 1-(3-dimethylaminopropyl)-3-ethylcarbodiimide hydrochloride or a carbonyldiimidazole such as CDI. Amide coupling additives, such as HOBt and HOAt can also be used to enhance the reaction. Additionally, uronium or phosphonium salts of non-nucleophilic anions, such as HBTU, HATU, PyBOP, and PyBrOP could be used in place of the more traditional coupling reagents. An additive such as dimethylaminopyridine may be used to enhance the reaction. In Step 3, substep 1, the protected carboxylic acid can be deprotected by methods well known in the art such as using an aqueous solution of lithium hydroxide in methanol or tetrahydrofuran to give the carboxylic acid. The acid product of substep 1, Step 3 can be reacted with the desired amine as described above to give the products of Formula Ia or alternatively the carboxylic acid compound of Step 3, substep 1 can be converted to the acid chloride and reacted with the desired amide as described above in Step 2, substep 2 to give compounds of Formula Ia. It should be pointed out that the amide coupling of the carboxylic acid product of Step 2 can be accomplished initially and then amide formation on the amine can be completed depending on artisan preference of the reactions to give compounds of Formula Ia.

A pharmaceutically acceptable salt of a compound of Formulas Ia can be formed by reaction of an appropriate free base of Formulas Ia with an appropriate pharmaceutically acceptable acid in a suitable solvent under standard conditions well known in the art. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

Preparation 1

Cis-(racemic)-Methyl-3-[tert-butoxycarbonyl(methyl)amino]cyclohexanecarboxylate

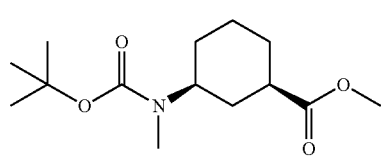

To a solution of cis-(racemic)-3-(tert-butoxycarbonylamino)cyclohexanecarboxylic acid (3 g, 12.33 mmol) in dimethylformamide is added sodium hydride (1.48 g, 36.99 mmol) at 0° C. under nitrogen. The mixture is warmed to room temperature and stirred for 1 hour and then it is cooled to 0° C. and methyl iodide (8.75 g, 61.65 mmol) is added drop wise. The mixture is stirred at room temperature for two days. To the mixture is added saturated NH₄Cl solution (150 mL) and the mixture is extracted with ethyl acetate (2×100 mL). The combined organic layers are washed with brine (3×100 mL), dried over Na₂SO₄, concentrated to give the title compound (3.34 g, 99.82%) as a yellow oil. The crude product is used directly without purification. LC/MS (m/z): 172 (M−100+1).

Preparation 2

Cis-(chiral)-Methyl-3-[tert-butoxycarbonyl(methyl) amino]cyclohexanecarboxylate, Isomer 1

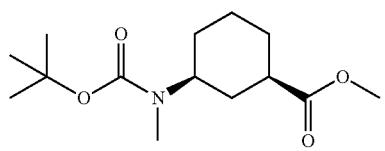 [SMILES: COC(=O)[C@@H]1CCC[C@H](N(C)C(=O)OC(C)(C)C)C1]

Cis-(racemic)-Methyl-3-[tert-butoxycarbonyl(methyl) amino]cyclohexanecarboxylate is purified by chiral SFC with the following conditions. SFC-200, Thar Waters, column: AY250 mm*50 mm, 10 μm, column temperature: 38° C., mobile phase:CO₂/isopropanol 90/10, flow rate: 180 g/min, detection wavelength: 220 nm to give Isomer 1: RT=2.3 min, 100% ee, LC-MS: 272 (M+H).

Preparation 3

Cis-(racemic)-Methyl-3-(methylamino)cyclohexanecarboxylate; 2,2,2-trifluoroacetic acid

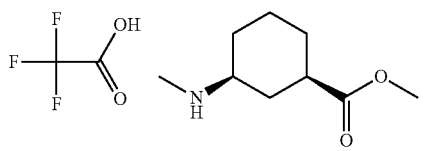

To a solution of cis-(racemic)-methyl-3-[(tert-butoxycarbonyl)(methyl)amino]cyclohexanecarboxylate (3.34 g, 12.31 mmol) in dichloromethane (20 mL) is added trifluoroacetic acid (10 mL, 132.25 mmol). The mixture is stirred at room temperature overnight. The mixture is concentrated to give the title compound (2.1 g, 99.63%) as a yellow oil. The crude product is used directly without purification. LC/MS (m/z): 172 (M+H).

Preparation 4

Cis-(racemic)-Methyl-3-[methyl-[3-(trifluoromethyl) benzoyl]amino]cyclohexanecarboxylate

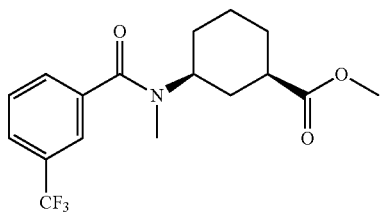 [SMILES: COC(=O)[C@@H]1CCC[C@H](N(C)C(=O)c2cccc(C(F)(F)F)c2)C1]

To a solution of cis-(racemic)-methyl-3-(methylamino) cyclohexanecarboxylate (2.1 g, 12.26 mmol) in dichloromethane (50 mL) is added triethylamine (3.72 g, 36.79 mmol). The mixture is cooled to 0° C. under N₂ and 3-trifluoromethylbenzoyl chloride (3.07 g, 14.72 mmol) is added drop wise. The mixture is warmed to room temperature and stirred for 3 hours. The mixture is concentrated and the residue is purified by silica gel chromatography (combiflash) eluting with petroleum ether/ethyl acetate from 100/0 to 60/40 to give the title compound (4.18 g, 99.27%) as a yellow oil. LC/MS (m/z): 344 (M+1).

Preparation 5

Cis-(racemic)-3-[Methyl-[3-(trifluoromethyl)benzoyl]amino]cyclohexanecarboxylic acid

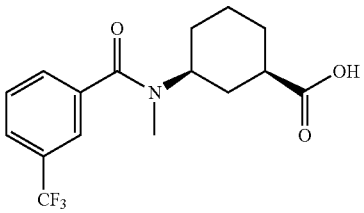 [SMILES: CN(C(=O)c1cccc(C(F)(F)F)c1)[C@H]1CCC[C@@H](C(=O)O)C1]

To a solution of cis-(racemic)-methyl-3-[methyl-[3-(trifluoromethyl)benzoyl]amino]cyclohexanecarboxylate (4.18 g, 12.17 mmol) in a mixture of tetrahydrofuran (20 mL), methanol (20 mL) and H₂O (20 mL), is added LiOH (2.55 g, 60.87 mmol). The mixture is stirred at room temperature overnight. The mixture is concentrated and the residue is dissolved in H₂O (100 mL). The mixture is washed with ethyl acetate (1×40 mL) and the pH adjusted to 2 with 1 M HCl solution. The mixture is extracted with ethyl acetate (2×100 mL). The combined organic layers are dried over Na₂SO₄ and concentrated to give the title compound (4 g, 99.77%) as a colorless oil. LC/MS (m/z): 330 (M+1).

Preparation 6

Cis-(racemic)-Methyl-3-[(3-chlorobenzoyl)-methyl-amino]cyclohexanecarboxylate

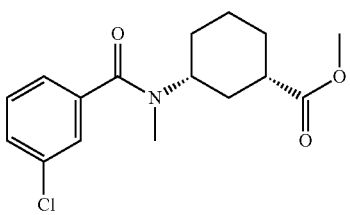 [SMILES: COC(=O)[C@H]1CCC[C@@H](N(C)C(=O)c2cccc(Cl)c2)C1]

To a solution of cis-(racemic) methyl-3-(methylamino)cyclohexanecarboxylate; 2,2,2-trifluoroacetic acid (2.13 g, 7.11 mmol) in dichloromethane (30 mL) is added triethylamine (2.88 g, 28.4 mmol). The mixture is cooled to 0° C. under $N_2$ and 3-chlorobenzoyl chloride (1.67 g, 9.24 mmol) is added drop wise. The mixture is warmed to room temperature and stirred for 1 hour. The mixture is concentrated and the residue is purified by silica gel chromatography (combi-flash) eluting with petroleum ether/ethyl acetate from 100/0 to 60/40 to give the title compound (1.73 g, 74.6%) as a white solid. LC/MS (m/z): 310 (M+H).

Preparation 7

Cis-(racemic)-Methyl-3-[(3-chlorobenzoyl)-methyl-amino]cyclohexanecarboxylic acid

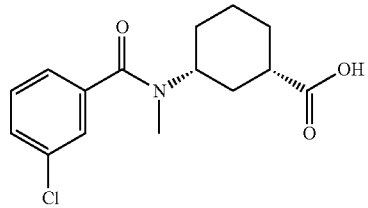 [SMILES: CN(C(=O)c1cccc(Cl)c1)[C@@H]1CCC[C@H](C(=O)O)C1]

To a solution of cis-(racemic)-methyl-3-[(3-chlorobenzoyl)-methyl-amino]cyclohexanecarboxylate (1.73 g, 5.31 mmol) in a mixture of tetrahydrofuran (10 mL), methanol (10 mL) and $H_2O$ (5 mL), is added LiOH (1.11 g, 26.5 mmol). The mixture is stirred at room temperature for 4 hours. The mixture is concentrated and the residue is dissolved in $H_2O$ (10 mL). The mixture is washed with ethyl acetate (1×20 mL) and the pH adjusted to 2 with 1 M HCl solution. The mixture is extracted with ethyl acetate (2×100 mL). The combined organic layers are dried over $Na_2SO_4$ and concentrated to give the title compound (1.5 g, 91%) as a white solid. LC/MS (m/z): 296 (M+H).

Preparation 8

Cis-(chiral)-Methyl-3-[methyl-[3-(trifluoromethoxy)benzoyl]amino]cyclohexanecarboxylate, Isomer 1

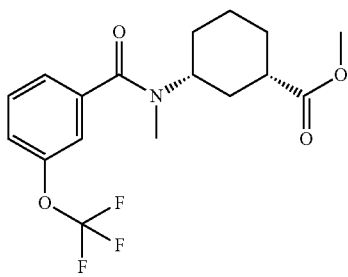 [SMILES: COC(=O)[C@H]1CCC[C@@H](N(C)C(=O)c2cccc(OC(F)(F)F)c2)C1]

To a solution of cis-(chiral)-methyl 3-(methylamino)cyclohexanecarboxylate, Isomer 1 (1.36 g, 7.94 mmol) in dichloromethane (30 mL), is added triethylamine (3.3 mL). The mixture is cooled to 0° C. under $N_2$, then 3-(trifluoromethoxy)benzoyl chloride (1.6 mL, 9.53 mmol) is added drop wise. The mixture is warmed to room temperature and stirred for 3 hours. The reaction mixture is evaporated in vacuo and the crude product is purified by silica gel flash chromatography to give the title compound (2.03 g, 69%) as yellow oil. LC/MS (m/z): 360 (M+H).

Preparation 9

Cis-(chiral)-3-[Methyl-[3-(trifluoromethoxy)benzoyl]amino]cyclohexanecarboxylic acid, Isomer 1

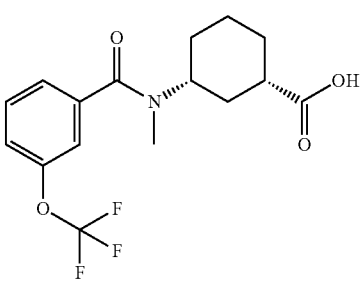

To a solution of cis-(chiral)-methyl-3-[methyl-[3-(trifluoromethoxy)benzoyl]amino]cyclohexanecarboxylate, Isomer 1 (800 mg, 2.2 mmol) in water (4 mL) and methanol (15 mL) is added lithium hydroxide (467 mg, 11.1 mmol). The mixture is stirred at room temperature overnight. The reaction mixture is evaporated in vacuo, and the residue is dissolved in water (3 mL) and ethyl acetate (3 mL). The pH is adjusted to pH=2 with 1 N HCl solution. The mixture is extracted with ethyl acetate (10 mL×2). The combined organic layers are washed with brine (5 mL), dried over $Na_2SO_4$, and evaporated to give the title compound (670 mg, 87%). LC/MS (m/z): 346 (M+H).

Preparation 10

Cis-(racemic)-Methyl-3-[benzyloxycarbonyl(methyl)amino]cyclohexanecarboxylate

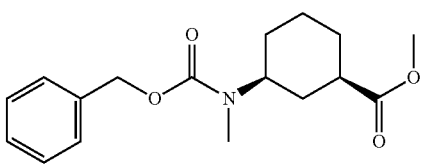

Sodium hydride (0.55 g, 13.75 mmol) is added to a solution of cis-methyl-3-(benzyloxycarbonylamino)cyclohexanecarboxylate (1.99 g, 6.83 mmol) in dimethylformamide (20 mL) at 0° C. under $N_2$ and stirred at ambient temperature. After 1 hour, the reaction mixture is cooled to 0° C., methyl iodide (2.96 g, 20.87 mmol) is added, and the reaction is warmed to ambient temperature. After 3 hours, saturated aqueous ammonium chloride is added and the mixture is extracted with ethyl acetate. The organic extracts are combined and washed with brine, dried over sodium sulfate, filtered, and concentrated under reduced pressure to give the title compound (1.13 g, 54%). MS (m/z): 306 (M+H).

Preparation 11

Cis-(chiral)-Methyl-3-[benzyloxycarbonyl(methyl)amino]cyclohexanecarboxylate, Isomer 1

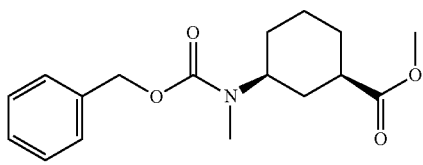 [SMILES: COC(=O)[C@@H]1CCC[C@H](N(C)C(=O)OCc2ccccc2)C1]

Cis-(racemic)-Methyl-3-[benzyloxycarbonyl(methyl)amino]cyclohexanecarboxylate is purified by chiral resolution to give Isomer 1: MS (m/z): 292 (M+H). >99% ee, RT=0.75 minutes (uv: 220 nm), LC column: 4.6×150 mm Chiralcel OD-H; column temperature: 40° C.; mobile phase gradient: 30% 3A ethanol: 70% $CO_2$; flow rate: 5.0 mL/minutes.

Preparation 12

Cis-(chiral)-3-[Benzyloxycarbonyl(methyl)amino]cyclohexanecarboxylic acid, Isomer 1

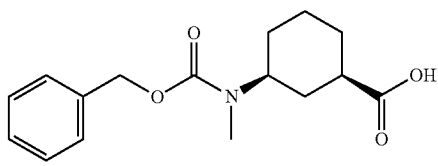 [SMILES: CN(C(=O)OCc1ccccc1)[C@H]1CCC[C@@H](C(=O)O)C1]

Lithium hydroxide (156.85 mg, 6.55 mmol) in water (0.5 mL) is added to a solution of cis-(chiral)-methyl-3-[benzyloxycarbonyl(methyl)amino]cyclohexanecarboxylate, Isomer 1 (0.4 g, 1.31 mmol) in methanol (5 mL) and the mixture is stirred at ambient temperature. After 7 hours, the reaction is concentrated to remove methanol, 3 N aqueous hydrochloric acid is added, and the reaction is extracted with ethyl acetate. The organic extracts are combined and concentrated under reduced pressure to give the title compound (0.35 g, 91%). MS (m/z): 292 (M+H).

Preparation 13

1-(2-Methoxyethyl)-4-methyl-5-nitro-imidazole

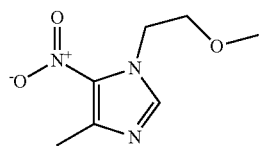

To a solution of 4-methyl-5-nitro-1H-imidazole (5.00 g, 39.3 mmol) in tetrahydrofuran (50 mL) is added 2-methoxyethanol (3.29 g, 43.3 mmol) and triphenylphosphine (15.6 g, 59.0 mmol) at 0° C. Diisopropyl azodicarboxylate (12.2 g, 59.0 mmol) is slowly added under $N_2$ and the mixture is stirred at room temperature overnight. The solvent is removed, the residue is diluted with $Et_2O$ (80 mL), filtered, and concentrated. The crude product is added to a solution of HCl (9 M, 40 mL) and the mixture is extracted with ethyl acetate (50 mL). The aqueous phase is adjusted to pH 8 with addition of $Na_2CO_3$ and the aqueous solution is extracted with ethyl acetate (2×80 mL). The organic extracts are combined, dried over $Na_2SO_4$, filtered, and concentrated to dryness. The residue is purified by silica gel chromatography eluting with petroleum ether to 1:2 petroleum ether to ethyl acetate to give the title compound (4 g, 54.9%) as a yellow oil. LC/MS (m/z): 186 (M+H).

Preparation 14

3-(2-Methoxyethyl)-5-methyl-imidazol-4-amine

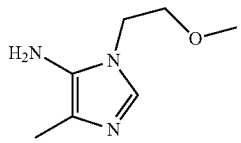

1-(2-methoxyethyl)-4-methyl-5-nitro-imidazole (4 g, 21.601 mmol) is added to tetrahydrofuran (150 mL) under a $N_2$ atmosphere followed by the addition of Raney nickel (2.53 g, 43.1 mmol). The mixture is stirred at room temperature for 1.5 hours. The mixture is filtered through a pad of diatomaceous earth and concentrated to dryness to give the title compound (3.35 g, 99.9%) as a brown oil. LC/MS (m/z): 156 (M+H).

Preparation 15

4-[2-(4-Methyl-5-nitro-imidazol-1-yl)ethyl]morpholine

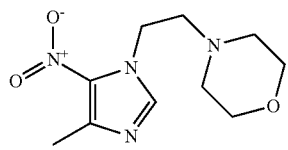 [SMILES: Cc1ncn(CCN2CCOCC2)c1[N+](=O)[O-]]

To a solution of 4-methyl-5-nitro-1H-imidazole (2.00 g, 15.7 mmol) in tetrahydrofuran (50 mL) is added 2-morpholinoethanol (2.27 g, 17.3 mmol) and triphenylphosphine (6.25 g, 23.6 mmol) at 0° C. Diisopropyl azodicarboxylate (4.87 g, 23.6 mmol) is slowly added under $N_2$. The mixture is stirred at room temperature for 3 days. The solvent is removed and the residue is diluted with $Et_2O$ (30 mL), filtered, and concentrated. The crude product is purified by silica gel chromatography eluting with petroleum ether to 1.2 petroleum ether and ethyl acetate to give the title compound (1 g, 26.5%) as a yellow oil. LC/MS (m/z): 241 (M+H).

Preparation 16

5-Methyl-3-(2-morpholinoethyl)imidazol-4-amine

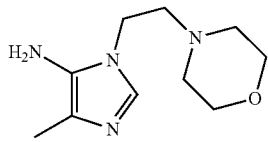

To a solution of 4-[2-(4-methyl-5-nitro-imidazol-1-yl)ethyl]morpholine (450 mg, 1.87 mmol) in tetrahydrofuran (25 mL) is added raney nickel (16.2 mg, 0.187 mmol) under $H_2$ and the mixture is stirred at room temperature for 2 hours under $H_2$. The mixture is filtered, washed with tetrahydrofuran (20 mL) and concentrated to dryness to give the title compound (0.36 g, 91.4%) as a yellow oil. LC/MS (m/z): 211 (M+H).

Preparation 17

Isopropyl 2-(4-methyl-5-nitro-imidazol-1-yl)acetate

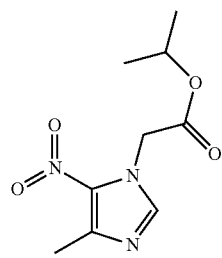 [SMILES: Cc1ncn(CC(=O)OC(C)C)c1[N+](=O)[O-]]

4-Methyl-5-nitro-1H-imidazole (5 g, 39.34 mmol), isopropyl bromoacetate (7.1 g, 39.34 mmol), potassium carbonate (1.5 equiv., 59.01 mmol), N,N-dimethylformamide (100 mL) are added together. The reaction is heated to 90° C. for 4 hours. The mixture is cooled to room temperature, quenched with NaCl (aq) and extracted with ethyl acetate. The combined organic phase is dried over anhydrous $Na_2SO_4$ and concentrated under reduced pressure. The residue is purified with silica gel flash chromatography on eluting with dichloromethane:methanol (20:1) to give the title compound (0.6 g, 7%) as white solid, which is the minor isomer. MS m/z 228.1 (M+H).

Preparation 18

Isopropyl 2-(5-amino-4-methyl-imidazol-1-yl)acetate

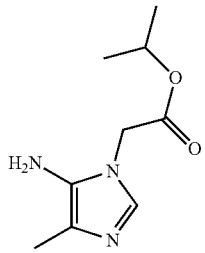

Isopropyl 2-(4-methyl-5-nitro-imidazol-1-yl)acetate (0.600 g, 2.64 mmol) is added to methanol (20 mL) followed by the addition of 10% palladium on carbon hydroxide (200 mg, 0.142 mmol). The mixture is degassed with $H_2$ and kept under balloon pressure of $H_2$ at 25° C. for 10 hours. The mixture is filtered over diatomaceous earth and concentrated to give slightly yellow oil as a crude product, which is used without further purification. MS m/z 198.1 (M+H).

Preparation 19

1-Isopropyl-4-methyl-5-nitro-imidazole

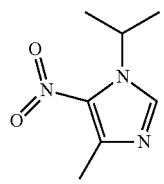

4-Methyl-5-nitro-1H-imidazole (1.2 g, 9.44 mmol) and N-methylpyrrolidone (15 mL) are added together at room temperature Sodium hydride (453.1 mg, 11.33 mmol) is added and the reaction is stirred for 10 minutes. Propane, 2-iodo-(1.04 mL, 10.39 mmol) is added and the mixture is stirred at room temperature for 3.5 hours. Water and ethyl acetate is added and the mixture is stirred until the phase is separated. The aqueous phase is extracted with ethyl acetate (50 mL) and the organic phase is washed with brine, dried with $Na_2SO_4$, and evaporated in vacuo. The residue is purified by silica gel flash chromatography eluting with 1:1 hexanes:ethyl acetate to give the title compound (320 mg, 18.03%) as a yellow oil. LC/MS (m/z): 170 (M+H).

Preparation 20

3-Isopropyl-5-methyl-imidazol-4-amine

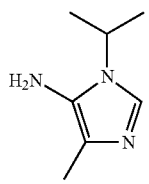

1-Isopropyl-4-methyl-5-nitro-imidazole (320 mg, 1.7 mmol), methanol (20 mL), 10% palladium on carbon (34 mg, 16.1 μmol) are added together. The mixture is degassed with $H_2$ and then stirred under balloon pressure of $H_2$ at room temperature for 5 hours. The mixture is filtered and concentrated, leading to slightly yellow oil, which is used without further purification. LC/MS (m/z): 140 (M+H).

Preparation 21

1-(Cyclopropylmethyl)-4-methyl-5-nitro-imidazole

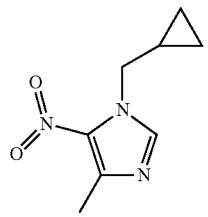

4-Methyl-5-nitro-1H-imidazole (1.2 g, 9.44 mmol), N-methylpyrrolidone (15 mL) are added together at room temperature. Sodium hydride (453.13 mg, 11.33 mmol) is added followed and the mixture is stirred 10 minutes. Cyclopropane, (bromomethyl)-(1.01 mL, 10.39 mmol) is added and the mixture is stirred at room temperature for 3.5 hours. Water and ethyl acetate is added, stirring until the phase is separated, and the aqueous phase is extracted with ethyl acetate (50 mL). The organic phase is washed with brine and dried with $Na_2SO_4$ and evaporated in vacuo. The residue is purified by silica gel flash chromatography eluting with 1:1 hexanes:ethyl acetate to give the title compound (524 mg, 21.44%) as a yellow oil. LC/MS (m/z): 182 (M+H)

Preparation 22

3-(Cyclopropylmethyl)-5-methyl-imidazol-4-amine

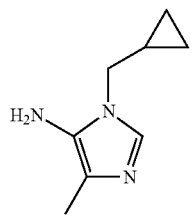

1-(Cyclopropylmethyl)-4-methyl-5-nitro-imidazole (523 mg, 1.7 mmol), methanol (20 mL), and 10% palladium on carbon (100 mg, 46.98 μmol) are added together. The mixture is degassed with $H_2$ and then stirred under balloon pressure of $H_2$ at room temperature for 5 hours. The mixture is filtered and concentrated, leading to slightly yellow oil, which is used without further purification. LC/MS (m/z): 152 (M+H).

Preparation 23

2-(4-Methyl-5-nitro-imidazol-1-yl)acetonitrile

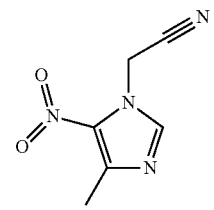

4-Methyl-5-nitro-1H-imidazole (2.4 g, 18.88 mmol), N-methylpyrrolidone (30 mL), and cesium carbonate (7.46 g, 22.66 mmol) are added together and stirred for 10 minutes at room temperature. Bromoacetonitrile (1.45 mL, 20.77 mmol) is added and the mixture is stirred at room temperature for 4 hours. Water and ethyl acetate is added and the mixture is stirred until the phase is separated. The aqueous phase is extracted with ethyl acetate (50 mL) and the organic phase is washed with brine, and dried with $Na_2SO_4$, and evaporated in vacuo. The residue is purified by silica gel flash chromatography eluting with 1:1 hexanes:ethyl acetate to give the title compound (435 mg, 12.48%) as a yellow solid. LC/MS (m/z): 167 (M+H)

Preparation 24

2-(5-Amino-4-methyl-imidazol-1-yl)acetonitrile

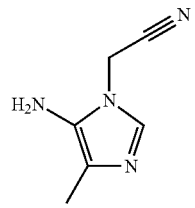

2-(4-Methyl-5-nitro-imidazol-1-yl)acetonitrile (156 mg, 892.0 μmol), methanol (15 mL), and 10% palladium on carbon (30 mg, 14.1 μmol) are added together. The mixture is degassed with $H_2$ and then stirred under balloon pressure of $H_2$ at room temperature for 3 hours. The mixture is filtered and concentrated, leading to slightly yellow oil, which is used for without further purification. LC/MS (m/z): 137 (M+H).

Preparation 25

4-Methyl-5-nitro-1-(2,2,2-trifluoroethyl)-1H-imidazole

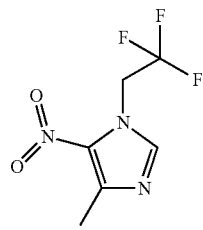

4-Methyl-5-nitro-1H-imidazole (10 g, 78.7 mmol), N-methylpyrrolidone (100 mL), and cesium carbonate (38.5 g, 118.0 mmol) are added together and stirred 10 minutes at room temperature. 2,2,2-Trifluoroethyl trifluoromethanesulfonate (19.2 mL, 82.6 mmol) is added and the mixture is stirred for 2 hours. Water and ethyl acetate is added, stirring until the phase is separated and the aqueous phase is extracted with ethyl acetate (300 mL*2), the combined organic phase is washed with brine and dried by $Na_2SO_4$, then evaporated in vacuo, the residue is purified by silica gel flash chromatography eluting with 1:1 hexanes:ethyl acetate to give the title compound (5.5 g, 33.43%) as a pink oil. LC/MS (m/z): 210 (M+H)

Preparation 26

5-Methyl-3-(2,2,2-trifluoroethyl)imidazol-4-amine

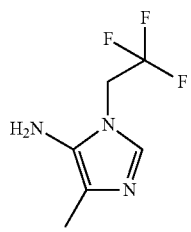

4-Methyl-5-nitro-1-(2,2,2-trifluoroethyl)-1H-imidazole (700 mg, 318.0 μmol), methanol (20 mL), and 10% palladium on carbon (140 mg, 131 μmol) are added together. The mixture is degassed with $H_2$ and then stirred under balloon pressure of $H_2$ at room temperature for 5 hours. The mixture is filtered and concentrated, leading to slightly yellow oil, which is used without further purification. LC/MS (m/z): 180 (M+H).

Preparation 27

2-(Cyclobutoxy)ethanol

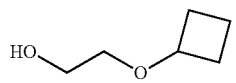

N-Butyllithium(2 mol/L) in cyclohexanes (19 mL, 38 mmol) is added drop wise to an ice-cold solution of cyclobutanol (2.6 g, 35 mmol) in tetrahydrofuran (60 mL) so as to maintain the reaction temperature below 10° C. The mixture is then stirred for 2 hours at 5-10° C. A solution of ethylenesulfate (4.9 g, 38 mmol) in tetrahydrofuran (20 mL) is added drop wise so as to maintain the reaction temperature below 15° C. Once the addition is complete, the reaction is stirred for a 3 hours at room temperature. Water (1 mL) followed by concentrated sulfuric acid in water (2 mL, 6.750 mol/L) is added and the reaction is stirred for an additional 18 hours at room temperature. The reaction mixture is neutralized by the addition of solid sodium bicarbonate, and the mixture is concentrated under reduced pressure. The residue is diluted with water and ethyl acetate, stirring until the two phases are separated. The aqueous phase is washed with ethyl acetate (2×80 mL), and the combined organic phases are washed with water (20 mL), brine (30 mL), dried with $Na_2SO_4$, evaporated in vacuo and the residue is purified by silica gel flash chromatography eluting with 5% to 10% methanol in dichloromethane to give the title compound (2.23 g, 49%) as a white solid. LC/MS (m/z): 117 (M+H).

Preparation 28

1-[2-(Cyclobutoxy)ethyl]-4-methyl-5-nitro-imidazole

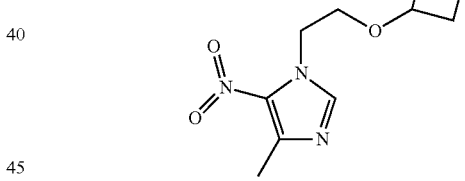

To a mixture of 4-methyl-5-nitroimidazole (1.90 g, 14.6 mmol) in tetrahydrofuran (40 mL) is added 2-(cyclobutoxy)ethanol (2.27 g, 17.6 mmol) and triphenylphosphine (4.66 g, 17.6 mmol). The reaction is cooled to 0° C. under $N_2$ and diisopropyl azodicarboxylate (3.49 mL, 17.6 mmol) is added drop wise. The mixture is warmed to room temperature and stirred overnight. The reaction is evaporated in vacuo and diethyl ether (50 mL) is added, stirring at room temperature for 30 minutes, and then filtered. The filter cake is washed with diethyl ether (50 mL), and the organic phase is washed with water (30 mL), brine (30 mL), dried by $Na_2SO_4$, and evaporated in vacuo. The crude product is purified by reverse phase flash chromatography eluting with 25% to 50% acetonitrile/water, 0.1% formic acid to give the title compound (1.74 g, 47.5%) as a yellow oil. LC/MS (m/z): 226 (M+H).

Preparation 29

3-[2-(Cyclobutoxy)ethyl]-5-methyl-imidazol-4-amine

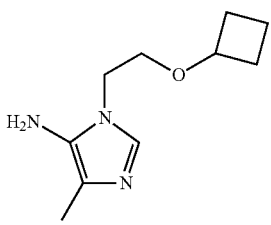

1-[2-(Cyclobutoxy)ethyl]-4-methyl-5-nitro-imidazole (0.641 g, 2.56 mmol), methanol (30 mL), and 10% palladium on carbon (120 mg, 56.4 µmol) are added together. The mixture is degassed with $H_2$ and then stirred under balloon pressure of $H_2$ at room temperature for 3 hours. The mixture is filtered and concentrated, leading to slightly yellow oil, which is used without further purification. LC/MS (m/z): 196 (M+H).

Preparation 30

4-Methyl-5-nitro-1-(oxetan-3-yl)imidazole

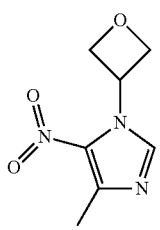

To a mixture of 4-methyl-5-nitroimidazole (3.0 g, 22.89 mmol) in tetrahydrofuran (40 mL) is added N,N-diisopropylethylamine (4.03 mL, 22.89 mmol), oxetan-3-ol (1.96 g, 25.18 mmol) and triphenylphosphine (6.67 g, 25.18 mmol). The reaction is cooled to 0° C. under $N_2$ and diethyl azodicarboxylate (4.3 mL, 27.47 mmol) is added drop wise. The mixture is warmed to room temperature and stirred overnight. The reaction is evaporated in vacuo and diethyl ether (50 mL) is added, stirring at room temperature for 30 minutes. The mixture is filtered, and the filter cake is washed with diethyl ether (50 mL). The combined organic phase is washed with water (30 mL), brine (30 mL), dried by $Na_2SO_4$, and evaporated in vacuo. The crude product is purified by reverse phase flash chromatography eluting with 25% to 50% acetonitrile/water, 0.1% formic acid to give the title compound (3.56 g, 59.4%) as a white solid. LC/MS (m/z): 184 (M+H).

Preparation 31

5-Methyl-3-(oxetan-3-yl)imidazol-4-amine

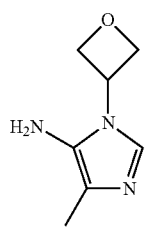

4-Methyl-5-nitro-1-(oxetan-3-yl)imidazole (530 mg, 2.03 mmol), methanol (20 mL), and 10% palladium on carbon (110 mg, 0.5 mmol) are added together. The mixture is degassed with $H_2$ and then stirred under balloon pressure of $H_2$ at room temperature for 4 hours. The mixture is filtered and concentrated to dryness, leading to a yellow solid, which is used for without further purification. LC/MS (m/z): 154 (M+H).

Preparation 32

4-Methyl-5-nitro-1-tetrahydropyran-4-yl-imidazole

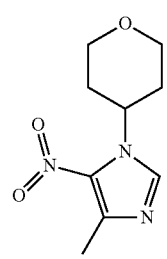

To a mixture of 4-methyl-5-nitroimidazole (2.50 g, 19.08 mmol) in tetrahydrofuran (40 mL) is added N,N-diisopropylethylamine (4.03 mL, 22.89 mmol), tetrahydro-4-pyranol (2.21 g, 20.99 mmol) and triphenylphosphine (5.56 g, 20.99 mmol). The reaction is cooled to 0° C. under $N_2$ and diethyl azodicarboxylate (5.6 mL, 22.19 mmol) is added drop wise. The mixture is warmed to room temperature and stirred overnight. The reaction is evaporated in vacuo. Diethyl ether (50 mL) is added and the mixture is stirred at room temperature for 30 minutes. The mixture is filtered, and the filter cake is washed with diethyl ether (50 mL), and the combined organic phase is washed with water (30 mL), brine (30 mL), dried by $Na_2SO_4$, and evaporated it in vacuo. The crude product is purified by reverse phase flash chromatography eluting with 25% to 50% acetonitrile/water, 0.1% formic acid to give the title compound (2.96 g, 54.8%) as a yellow oil. LC/MS (m/z): 212 (M+H).

Preparation 33

5-Methyl-3-tetrahydropyran-4-yl-imidazol-4-amine

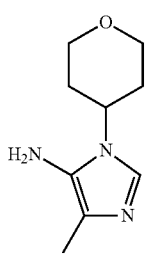

4-Methyl-5-nitro-1-tetrahydropyran-4-yl-imidazole (1.73 g, 6.55 mmol), methanol (50 mL), and 10% palladium on carbon (320 mg, 0.15 mmol) are added together. The mixture is degassed with $H_2$ and then stirred under a balloon pressure of $H_2$ at room temperature for 5 hours. The mixture is filtered and concentrated, leading to slightly yellow oil, which is used without further purification. LC/MS (m/z): 182 (M+H).

Preparation 34

4-Methyl-1-(1-methylazetidin-3-yl)-5-nitro-imidazole

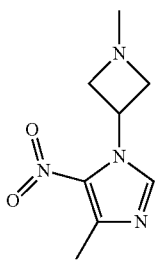

To a mixture of 4-methyl-5-nitroimidazole (4.0 g, 31 mmol) in tetrahydrofuran (100 mL) is added 1-methylazetidin-3-ol (3.0 g, 35 mmol) and triphenylphosphine (9.9 g, 38 mmol), the reaction is cooled to 0° C. under $N_2$ and diisopropyl azodicarboxylate (6.2 mL, 31 mmol) is added drop wise. The mixture is warmed to room temperature and stirred overnight. The reaction is evaporated in vacuo and diethyl ether (50 mL) is added and the mixture is stirred at room temperature for 30 minutes. The mixture is filtered and the filter cake is washed with diethyl ether (50 mL). The combined organic phase is washed with water (30 mL), brine (30 mL), dried with $Na_2SO_4$, and evaporated in vacuo. The crude product is purified by reverse phase flash chromatography eluting with 25% to 50% acetonitrile/water, 0.1% formic acid to give the title compound (4.8 g, 78%) as a yellow oil. LC/MS (m/z): 197 (M+H).

Preparation 35

5-Methyl-3-(1-methylazetidin-3-yl)imidazol-4-amine

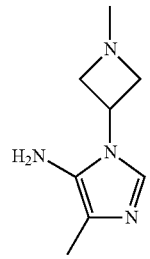

4-Methyl-1-(1-methylazetidin-3-yl)-5-nitro-imidazole (1.60 g, 8.155 mmol), tetrahydrofuran (50 mL), and 10% palladium on carbon hydroxide (600 mg, 0.42 mmol) are added together. The mixture is degassed with $H_2$ and then stirred under a balloon pressure of $H_2$ at room temperature for 15 hours. The mixture is filtered and concentrated to a yellow oil, which is used without further purification. LC/MS (m/z): 167 (M+H).

Preparation 36

1-(2,2-Difluoroethyl)-4-methyl-5-nitro-imidazole

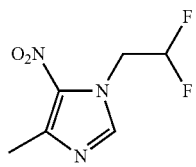

To a solution of 4-methyl-5-nitro-1H-imidazole (6 g, 47.2 mmol) in tetrahydrofuran (100 mL) is added difluoroethanol (4.3 g, 52.2 mmol) and triphenylphosphine (18.8 g, 70.8 mmol) at 0° C. under $N_2$, then diisopropyl azodicarboxylate (17.2 g, 85.0 mmol) is added drop wise. The mixture is allowed to warm to room temperature and stirred overnight. The mixture is concentrated and diethyl ether (250 mL) is added. The solid is removed and washed with diethyl ether. The organic wash concentrated and the residue is purified by silica gel chromatography (combi-flash) eluting with 100% ethyl acetate to 3:1 ethyl acetate:petroleum ether to give the crude product. The mixture is diluted with diethyl ether (50 mL), and filtered. The filtrate is concentrated to give the title compound (5.0 g, 55%) as a white solid. LC/MS (m/z): 192 (M+H).

Preparation 37

3-(2,2-Difluoroethyl)-5-methyl-imidazol-4-amine

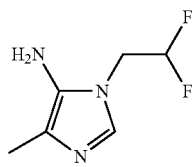

To a solution of 1-(2,2-difluoroethyl)-4-methyl-5-nitro-imidazole (0.5 g, 2.6 mmol) in ethyl acetate (15 mL) under H₂, is added 5% palladium on carbon (0.1 g) at room temperature. The mixture is stirred for 18 hours, filtered to remove the palladium catalyst, and concentrated to give the title compound (0.38 g, 90%). LC/MS (m/z): 162 (M+H).

Preparation 38

Cis-(chiral)-Benzyl N-[3-[[3-(2,2-difluoroethyl)-5-methyl-imidazol-4-yl]carbamoyl]cyclohexyl]-N-methyl-carbamate, Isomer 1

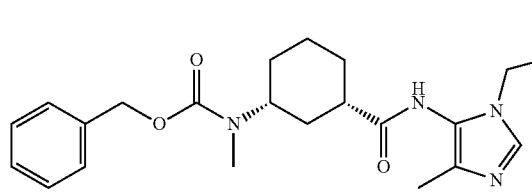

To a solution of cis-(chiral)-3-[benzyloxycarbonyl(methyl)amino]cyclohexanecarboxylic acid, Isomer 1 (1.2 g, 4.0 mmol) and 3-(2,2-difluoroethyl)-5-methyl-imidazol-4-amine (0.97 g, 6.0 mmol) in pyridine (30 mL), is added 1-(3-dimethylaminopropyl)-3-ethylcarbodiimide hydrochloride (1.2 g, 6.0 mmol) and the reaction is warmed to 60° C. The solution is concentrated and purified with silica gel flash chromatography eluting with 15/1, dichloromethane/methanol to give the title compound (0.63 g, 36%). LC/MS (m/z): 435 (M+H).

Preparation 39

Cis-(chiral)-(N-[3-(2,2-Difluoroethyl)-5-methyl-imidazol-4-yl]-3-(methylamino)cyclohexanecarboxamide, Isomer 1

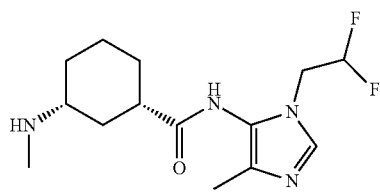

To a solution of cis-(chiral)-benzyl N-[3-[[3-(2,2-difluoroethyl)-5-methyl-imidazol-4-yl]carbamoyl]cyclohexyl]-N-methyl-carbamate, Isomer 1 (0.63 g, 1.4 mmol) in methanol (20 mL) is added 5% Pd/C (0.15 g) at room temperature under H₂. The reaction is stirred until completion and the solution is filtered to remove Pd/C, concentrated, and dried to give the title compound (0.42 g, 96%). LC/MS (m/z): 301 (M+H).

Example 1

Cis-(chiral)-N-[3-[(3,5-Dimethylimidazol-4-yl)carbamoyl]cyclohexyl]-N-methyl-3-(trifluoromethyl)benzamide, isomer 1

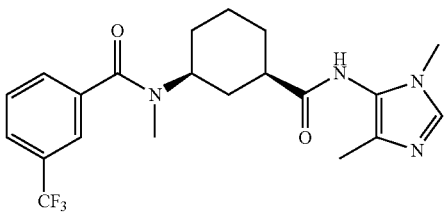 [SMILES: Cc1ncn(C)c1NC(=O)[C@@H]1CCC[C@H](N(C)C(=O)c2cccc(C(F)(F)F)c2)C1]

To a solution of cis-(racemic)-3-[methyl-[3-(trifluoromethyl)benzoyl]amino]cyclohexanecarboxylic acid (0.4 g, 1.09 mmol) in pyridine (10 mL) is added 3,5-dimethylimidazol-4-amine hydrochloride (249.52 mg, 1.64 mmol) and 1-(3-dimethylaminopropyl)-3-ethylcarbodiimide hydrochloride (523.91 mg, 2.73 mmol). The mixture is stirred at 58° C. for 22 hours. Then the mixture is concentrated and the crude product is purified by preparative HPLC to give the racemic title compound, which is resolved with chiral chromatography to give the title compound as the first eluting isomer, (0.0889 g, 19.15%) as a light yellow solid. LC/MS (m/z): 432 (M+1), 100% ee, RT=1.58 minutes (UV), Instrument: SFC-80 (Thar, Waters), column: AD-H 20×250 mm, 5 μm (Regis), column temperature: 35° C., mobile phase: CO₂/methanol (0.1% diethylamine)=75/25, flow rate: 80 g/min, back pressure: 100 bar, detection wavelength: 214 nm, cycle time: 4.4 min, sample solution: 250 mg dissolved in 40 mL methanol, injection volume: 5 mL.

Example 2

Cis-(chiral) N-methyl-N-3-((4-methyl-1-(2,2,2-trifluoroethyl)-1H-imidazol-5-yl)carbamoyl)cyclohexyl)-3-(trifluoromethoxy)benzamide, Isomer 1

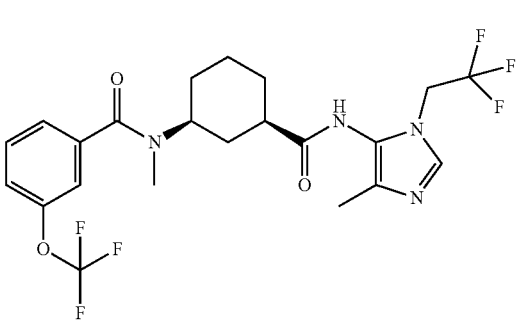 [SMILES: Cc1ncn(CC(F)(F)F)c1NC(=O)[C@@H]1CCC[C@H](N(C)C(=O)c2cccc(OC(F)(F)F)c2)C1]

Cis-(chiral)-3-[Methyl-[3-(trifluoromethoxy)benzoyl]amino]cyclohexanecarboxylic acid, Isomer 1 (0.2 g, 0.58 mmol), 4-methyl-1-(2,2,2-trifluoroethyl)-1H-imidazol-5- amine (114.13 mg, 1.55 mmol), 1-(3-dimethylaminopropyl)-3-ethylcarbodiimide hydrochloride (277.58 mg, 1.45 mmol), and pyridine (5 mL) are added together and stirred at 50° C. for 20 hours. The mixture is concentrated under reduced pressure and the residue is purified by preparative HPLC eluting with 17-37% CH$_3$CN in water, 0.1% formic acid to give the title compound (31 mg, 10.57%) as white solid. MS (m/z): 507.1 [M+H]$^+$.

Example 3

Cis-(chiral) N-Methyl-N-3-((4-methyl-1-(1-methylazetidin-3-yl)-1H-imidazol-5-yl) carbamoyl)cyclohexyl)-3-(trifluoromethoxy)benzamide, Isomer 1

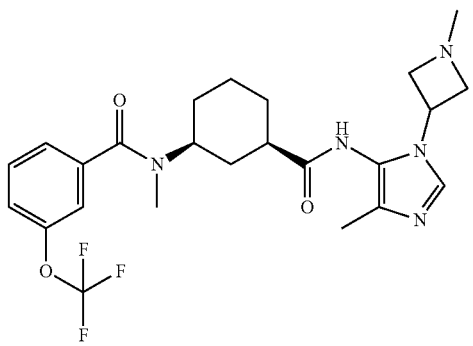 [SMILES: Cc1ncn(C2CN(C)C2)c1NC(=O)[C@@H]1CCC[C@H](N(C)C(=O)c2cccc(OC(F)(F)F)c2)C1]

Cis-(chiral)-3-[Methyl-[3-(trifluoromethoxy)benzoyl]amino]cyclohexanecarboxylic acid, Isomer 1 (0.70 g, 2.027 mmol), 5-methyl-3-(1-methylazetidin-3-yl)imidazol-4-amine (672 mg, 4.04 mmol), 1-(3-dimethylaminopropyl-3-ethylcarbodiimide hydrochloride (700 mg, 3.65 mmol), and pyridine (50 mL) are added together. The reaction is stirred at 60° C. for 56 hours. The mixture is concentrated and purified through silica gel flash chromatography eluting with dichloromethane and methanol 20:1 to give the product (210 mg), which is then purified through preparative HPLC eluting with 3% CH$_3$CN in water, 0.1% formic acid to give the title compound (32.0 mg, 3.04%) as slightly yellow solid. MS (m/z): 493.2[M+H]$^+$.

The following Example is prepared essentially by the method of Example 3.

Example 5

Cis-(chiral)-N-3-((1-(2,2-Difluoroethyl)-4-methyl-1H-imidazol-5-yl)carbamoyl)cyclohexyl)-3-fluoro-N-methyl-5-(trifluoromethyl)benzamide, Isomer 1

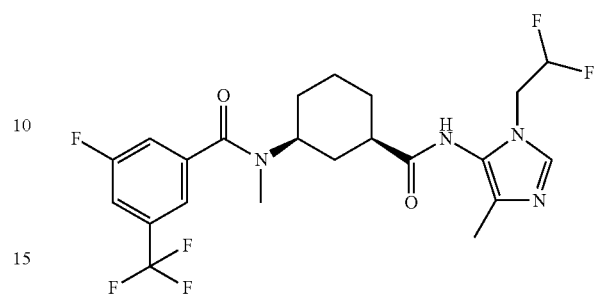

3-Fluoro-5-(trifluoromethyl)benzoic acid (415 mg, 1.19 mmol), dichloromethane (50.0 mL), oxalyl chloride (151 mg, 1.19 mmol) are added together at 0° C., 10 drops of N,N-dimethylformamide (0.01 equiv.) is added drop wise. The mixture is warmed to 25° C. and stirred for 2 hours. The solvent is removed under reduced pressure. N-[3-(2,2-Difluoroethyl)-5-methyl-imidazol-4-yl]-3-(methylamino) cyclohexanecarboxamide, Isomer 1 (300 mg, 0.9987 mmol), dichloromethane (50.0 mL) and triethylamine (1.99 mmol) are added to the acyl chloride formed above. The mixture is stirred at 25° C. for 16 hours. The mixture is concentrated and purified through silica gel flash chromatography eluting with 10:1 dichloromethane/methanol to give a yellow solid which is further purified through preparative HPLC eluting with 14-29% CH$_3$CN in water, 0.1% formic acid to give the title product (170 mg, 34.71%) as white solid. MS (m/z): 435.1 [M+H]$^+$.

Example 6

Cis-(chiral)-N-[-3-[(3-Isopropyl-5-methyl-imidazol-4-yl)carbamoyl]cyclohexyl]-N-methyl-3-(trifluoromethyl)benzamide, Isomer 1

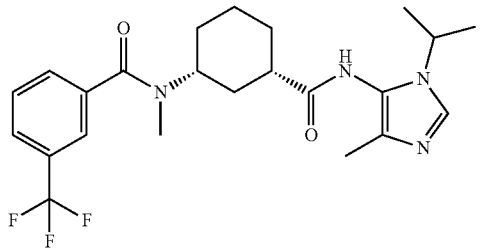 [SMILES: Cc1ncn(C(C)C)c1NC(=O)[C@H]1CCC[C@@H](N(C)C(=O)c2cccc(C(F)(F)F)c2)C1]

| Ex # | Chemical Name | Structure | ES/MS (m/z) (M + H) |
|---|---|---|---|
| 4 | Cis-(chiral)-Isopropyl 2-(4-methyl-5-(3-(N-methyl-3-(trifluoromethyl)benzamido) cyclohexanecarboxamido)-1H-imidazol-1-yl)acetate, Isomer 1 | 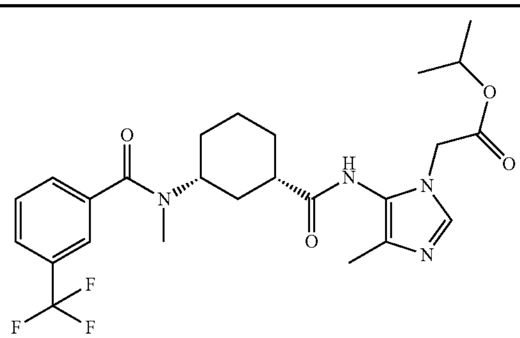 | 509 |

To a solution of cis-(chiral)-3-[methyl-[3-(trifluoromethyl)benzoyl]amino]cyclohexanecarboxylic acid, Isomer 1 (160 mg, 485.9 µmol) in dichloromethane (20.0 mL) is added 3-isopropyl-5-methyl-imidazol-4-amine (150.3 mg, 971.7 µmol), HATU (406.4 mg, 1.1 mmol) and diisopropylethylamine (288.1 µL, 1.7 mmol). The mixture is stirred at room temperature overnight. Then the mixture is concentrated and the crude product is purified by silica gel flash chromatography eluting with 5% MeOH in dichloromethane followed by purification with preparative HPLC eluting with 30-40% acetonitrile in water, 10 mM NH$_4$HCO$_3$ to give the title compound (2.7 mg, 1.11%) as a white solid. LC/MS (m/z): 451 (M+H).

Example 7

Cis-(chiral)-N-[-3-[[3-(Cyclopropylmethyl)-5-methyl-imidazol-4-yl]carbamoyl]cyclohexyl]-N-methyl-3-(trifluoromethyl)benzamide, Isomer 1

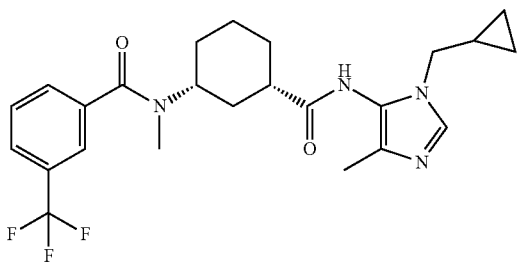 [SMILES: Cc1ncn(CC2CC2)c1NC(=O)[C@H]1CCC[C@@H](N(C)C(=O)c2cccc(C(F)(F)F)c2)C1]

To a solution of cis-(chiral)-3-[methyl-[3-(trifluoromethyl)benzoyl]amino]cyclohexanecarboxylic acid, Isomer 1 (145 mg, 440.3 µmoles) in dichloromethane (20.0 mL) is added 3-(cyclopropylmethyl)-5-methyl-imidazol-4-amine (190.2 mg, 880.6 µmol), HATU (368.3 mg, 968.7 µmol) and diisopropylethylamine (261.1 µL, 1.5 mmol). The mixture is stirred at room temperature overnight. The mixture is concentrated and the crude product is purified by silica gel flash chromatography eluting with 5% to 10% methanol in dichloromethane followed by preparative HPLC eluting with 32-42% acetonitrile in water, 10 mM NH$_4$HCO$_3$ to give the title compound (3.1 mg, 1.37%) as a white solid. LC/MS (m/z): 463 (M+H).

Example 8

Cis-(chiral)-N-[3-[[3-(cyanomethyl)-5-methyl-imidazol-4-yl]carbamoyl]cyclohexyl]-N-methyl-3-(trifluoromethyl)benzamide, Isomer 1

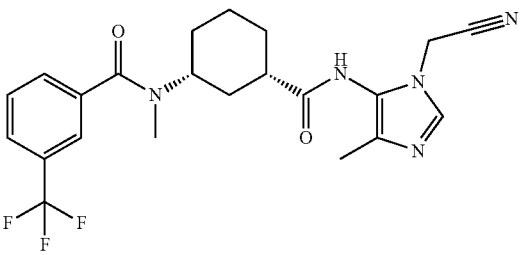 [SMILES: Cc1ncn(CC#N)c1NC(=O)[C@H]1CCC[C@@H](N(C)C(=O)c2cccc(C(F)(F)F)c2)C1]

To a solution of cis-(chiral)-3-[methyl-[3-(trifluoromethyl)benzoyl]amino]cyclohexanecarboxylic acid, Isomer 1 (230 mg, 663.5 µmol) in pyridine (10 mL) is added 2-(5-amino-4-methyl-imidazol-1-yl)acetonitrile (133.1 mg, 928.9 µmol) and 1-(3-dimethylaminopropyl)-3-ethylcarbodiimide hydrochloride (327.8 mg, 1.7 mmol). The mixture is stirred at 50° C. for 22 hours. The mixture is concentrated and the crude product is purified by silica gel flash chromatography eluting with 5% to 10% methanol in dichloromethane followed by preparative HPLC eluting with 30-40% acetonitrile in water, 10 mM NH$_4$HCO$_3$ to give the title compound (39.0 mg, 12.48%) as a pale yellow solid. LC/MS (m/z): 448 (M+H).

The following Example is prepared essentially by the method of Example 8.

| Ex # | Chemical Name | Structure | ES/MS (m/z) (M + H) |
|---|---|---|---|
| 9 | Cis-(chiral)-N-[3-[[3-(2,2-Difluoroethyl)-5-methyl-imidazol-4-yl]carbamoyl]cyclohexyl]-N-methyl-3-(trifluoromethyl)benzamide, Isomer 1 | 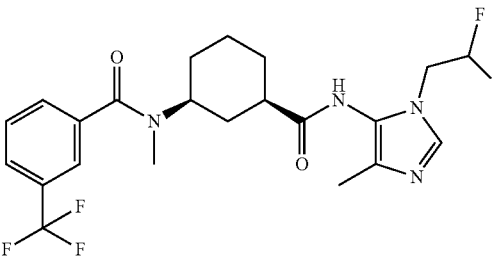 | 473 |

Example 10

Cis-(chiral)-N-Methyl-N-[3-[[5-methyl-3-(2,2,2-trifluoroethyl)imidazol-4-yl]carbamoyl]cyclohexyl]-3-(trifluoromethyl)benzamide, Isomer 1

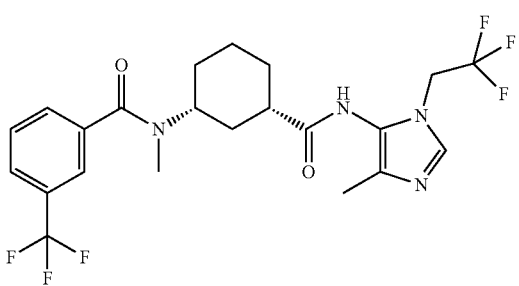 [SMILES: Cc1ncn(CC(F)(F)F)c1NC(=O)[C@H]1CCC[C@@H](N(C)C(=O)c2cccc(C(F)(F)F)c2)C1]

To a solution of added cis-(chiral)-3-[methyl-[3-(trifluoromethyl)benzoyl]amino]cyclohexanecarboxylic acid, Isomer 1 (700 mg, 2.02 mmol) in pyridine (10 mL) is added 5-methyl-3-(2,2,2-trifluoroethyl)imidazol-4-amine (578.8 mg, 3.23 mmol) and 1-(3-dimethylaminopropyl)-3-ethylcarbodiimide hydrochloride (718.4 mg, 3.64 mmol). The mixture is stirred at 50° C. for 22 hours. The mixture is concentrated and the crude product is purified by preparative HPLC eluting with 15-35% acetonitrile in water, 0.1% formic acid to give the title compound (310 mg, 29.74%) as a white solid. LC/MS (m/z): 491 (M+H).

Example 11

Cis-(chiral)-N-[3-[[3-[2-(Cyclobutoxy)ethyl]-5-methyl-imidazol-4-yl]carbamoyl]cyclohexyl]-N-methyl-3-(trifluoromethyl)benzamide, Isomer 1

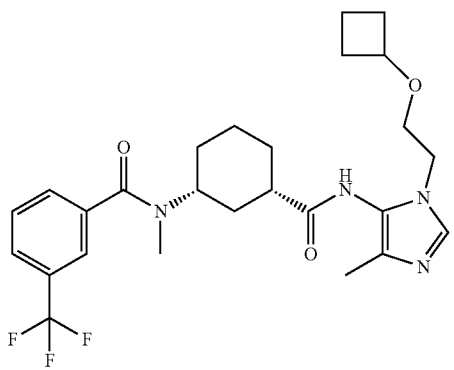 [SMILES: Cc1ncn(CCOC2CCC2)c1NC(=O)[C@H]1CCC[C@@H](N(C)C(=O)c2cccc(C(F)(F)F)c2)C1]

To a solution of cis-(chiral)-3-[methyl-[3-(trifluoromethyl)benzoyl]amino]cyclohexanecarboxylic acid, Isomer 1 (250 mg, 721.2 μmol) in pyridine (10 mL) is added 3-[2-(cyclobutoxy)ethyl]-5-methyl-imidazol-4-amine (273.8 mg, 1.26 mmol) and 1-(3-dimethylaminopropyl)-3-ethylcarbodiimide hydrochloride (256.6 mg, 1.30 mmol). The mixture is stirred at 60° C. for 2.5 hours. Then the mixture is concentrated and the crude product is purified by silica gel flash chromatography eluting with 5% to 10% methanol in dichloromethane followed by preparative HPLC eluting with 19-34% acetonitrile in water, 0.1% formic acid to give the title compound (140.0 mg, 36.40%) as a pale yellow solid. LC/MS (m/z): 507 (M+H).

Example 12

Cis-(chiral)-N-methyl-N-[3-[(5-methyl-3-tetrahydropyran-4-yl-imidazol-4-yl) carbamoyl]cyclohexyl]-3-(trifluoromethyl)benzamide, Isomer 1

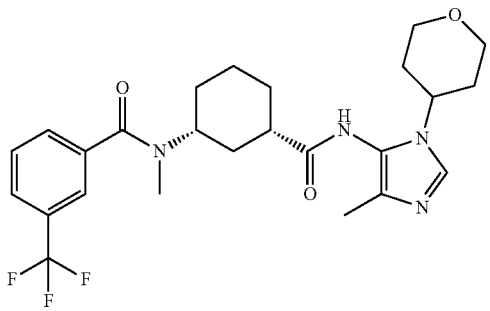 [SMILES: Cc1ncn(C2CCOCC2)c1NC(=O)[C@H]1CCC[C@@H](N(C)C(=O)c2cccc(C(F)(F)F)c2)C1]

To a solution of cis-(chiral)-3-[methyl-[3-(trifluoromethyl)benzoyl]amino]cyclohexanecarboxylic acid, Isomer 1 (1050 mg, 3.03 mmol) in pyridine (40 mL) is added 5-methyl-3-tetrahydropyran-4-yl-imidazol-4-amine (1.37 g, 6.06 mmol) and 1-(3-dimethylaminopropyl)-3-ethylcarbodiimide hydrochloride (1.20 g, 6.06 mmol). The mixture is stirred at 60° C. overnight. The mixture is concentrated and the crude product is purified by silica gel flash chromatography eluting with 5% to 15% methanol in dichloromethane followed by preparative HPLC eluting with 11-31% acetonitrile in water, 0.1% formic acid to give the title compound (440.0 mg, 28.02%) as a white solid. LC/MS (m/z): 493 (M+H).

Example 13

Cis-(chiral)-N-Methyl-N-[(cis)-3-[(5-methyl-3-tetrahydropyran-4-yl-imidazol-4-yl)carbamoyl]cyclohexyl]-3-(trifluoromethoxy)benzamide, Isomer 1

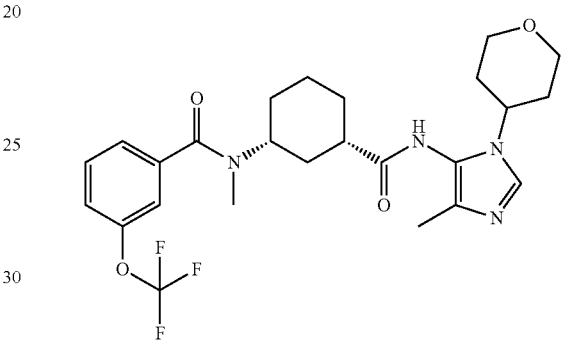

To a solution of cis-(chiral)-3-[methyl-[3-(trifluoromethoxy)benzoyl]amino]cyclohexanecarboxylic acid, Isomer 1 (0.200 g, 0.58 mmol) in pyridine (20 mL) is added 5-methyl-3-tetrahydropyran-4-yl-imidazol-4-amine (0.23 g, 1.01 mmol) and 1-(3-dimethylaminopropyl)-3-ethylcarbodiimide hydrochloride (0.206 g, 1.04 mmol). The mixture is stirred at 60° C. overnight. Then the mixture is concentrated and the crude product is purified by silica gel flash chromatography eluting with 5% to 15% methanol in dichloromethane followed by preparative HPLC eluting with 11-31% acetonitrile in water, 0.1% TFA to give the title compound (13 mg; 3.97%) as a white solid. LC/MS (m/z): 509 (M+H).

Example 14

Cis-(chiral)-N-Methyl-N-[3-[[5-methyl-3-(1-methyl-azetidin-3-yl)imidazol-4-yl]carbamoyl]cyclohexyl]-3-(trifluoromethyl)benzamide, Isomer 1

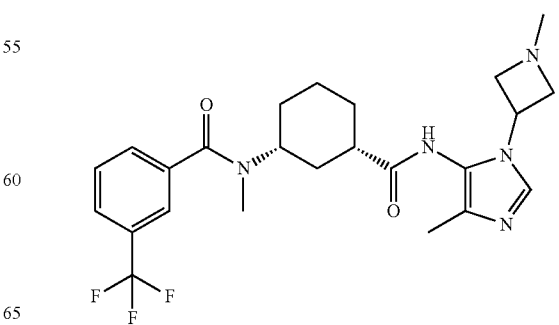

To a solution of cis-(chiral)-3-[methyl-[3-(trifluoromethyl)benzoyl]amino]cyclohexanecarboxylic acid, Isomer 1 (500 mg, 1.44 mmol) in pyridine (40 mL) is added 5-methyl-3-(1-methylazetidin-3-yl)imidazol-4-amine (504.8 mg, 2.88 mmol) and 1-(3-dimethylaminopropyl)-3-ethylcarbodiimide hydrochloride (570.2 mg, 2.88 mmol). The mixture is stirred at 60° C. overnight. The mixture is concentrated and the crude product is purified by silica gel flash chromatography eluting with 5% to 15% methanol in dichloromethane followed by preparative HPLC eluting with 3-20% acetonitrile in water, 0.1% formic acid to give the title compound (23.0 mg, 3.17%) as an orange solid. LC/MS (m/z): 478 (M+H).

Example 15

Cis-(chiral)-N-Methyl-N-[-3-[[5-methyl-3-(oxetan-3-yl)imidazol-4-yl]carbamoyl]cyclohexyl]-3-(trifluoromethyl)benzamide, Isomer 1

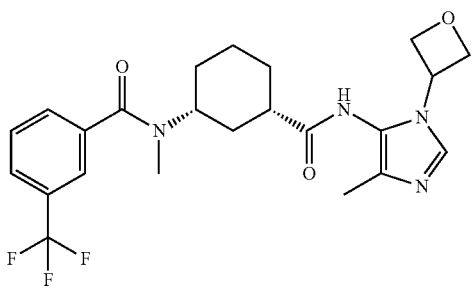 [SMILES: Cc1ncn(C2COC2)c1NC(=O)[C@H]1CCC[C@@H](N(C)C(=O)c2cccc(C(F)(F)F)c2)C1]

To a solution of cis-(chiral)-3-[methyl-[3-(trifluoromethyl)benzoyl]amino]cyclohexane carboxylic acid, Isomer 1 (350 mg, 1.01 mmol) in pyridine (20 mL) is added 5-methyl-3-(oxetan-3-yl)imidazol-4-amine (442 mg, 2.02 mmol) and 1-(3-dimethylaminopropyl)-3-ethylcarbodiimide hydrochloride (399 mg, 2.02 mmol). The mixture is stirred at 60° C. overnight. The mixture is concentrated and the crude product is purified by silica gel flash chromatography eluting with 5% to 15% methanol in dichloromethane followed by preparative HPLC eluting with 12-32% acetonitrile in water, 0.1% formic acid to give the title compound (198.0 mg, 40.11%) as a pale yellow solid. LC/MS (m/z): 465 (M+H).

Example 16

Cis-(chiral)-3-Chloro-N-[3-[[3-(2,2-difluoroethyl)-5-methyl-imidazol-4-yl]carbamoyl]cyclohexyl]-N-methyl-benzamide, Isomer 1

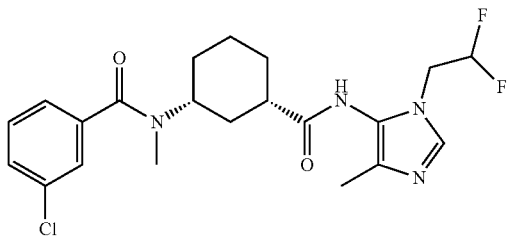 [SMILES: Cc1ncn(CC(F)F)c1NC(=O)[C@H]1CCC[C@@H](N(C)C(=O)c2cccc(Cl)c2)C1]

To a solution of cis-(racemic)-3-[methyl-[(3-chlorobenzoyl)amino]cyclohexane carboxylic acid (650 mg, 2.09 mmol) in pyridine (10 mL) is added 3-(2,2-difluoroethyl)-5-methyl-imidazol-4-amine (561 mg, 3.13 mmol) and 1-(3-dimethylaminopropyl)-3-ethylcarbodiimide hydrochloride (743 mg, 3.76 mmol). The mixture is stirred at 60° overnight. The mixture is concentrated and the crude product is purified by silica gel flash chromatography eluting with 5% to 15% methanol in dichloromethane followed by preparative HPLC eluting with 12-32% acetonitrile in water, 0.1% formic acid to give the title compound (660.0 mg, 64.83%) as a white solid, which is resolved with chiral chromatography utilizing the following conditions: Instrument: SFC-80 (Thar, Waters), column: AD-H 20*250 mm, 5 μm (Daicel), column temperature: 35° C., mobile phase: $CO_2$/MeOH=65/35, flow rate: 80 g/min, back pressure: 100 bar, detection wavelength: 214 nm, cycle time: 4.8 min, sample solution: 660 mg dissolved in 48 mL methanol, injection volume: 5 mL to give the title compound as the first eluting isomer (162 mg, 25.9%). LC/MS (m/z): 439 (M+H), 100% ee, RT=1.98 minutes, Example 17

Cis-(chiral)-N-3-[[3-(2-methoxyethyl)-5-methyl-imidazol-4-yl]carbamoyl]cyclohexyl]-N-methyl-3-(trifluoromethyl)benzamide, Isomer 1

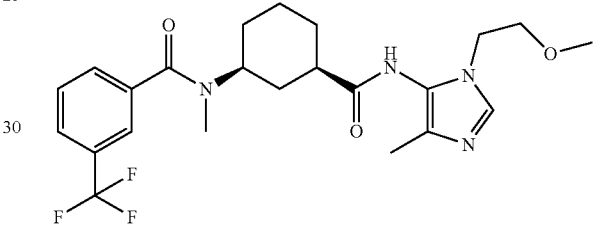

To a solution of cis-(chiral)-3-[methyl-[3-(trifluoromethyl)benzoyl]amino]cyclohexane carboxylic acid, Isomer 1 (2 g, 6.073 mmol) and 3-(2-methoxyethyl)-5-methyl-imidazol-4-amine (2.357 g, 15.18 mmol) in pyridine (50 mL) is added 1-(3-dimethylaminopropyl)-3-ethylcarbodiimide hydrochloride (2.851 g, 14.58 mmol) under $N_2$ and the mixture is stirred at room temperature for 3 days. The mixture is concentrated in vacuo and dissolved in dichloromethane (150 mL), washed with water (3×150 mL), dried over anhydrous $Na_2SO_4$, and purified by silica gel combiflash chromatography eluting with 0~7% methanol in dichloromethane with 1% $NH_4OH$. The product is further purified by prep-HPLC to give the title compound as a light yellow solid (0.419 g, 14.36%). LC/MS (m/z): 467 (M+H).

Example 18

Cis-(chiral)-N-Methyl-N-3-[[5-methyl-3-(2-morpholinoethyl)imidazol-4-yl]carbamoyl]cyclohexyl]-3-(trifluoromethyl)benzamide, Isomer 1

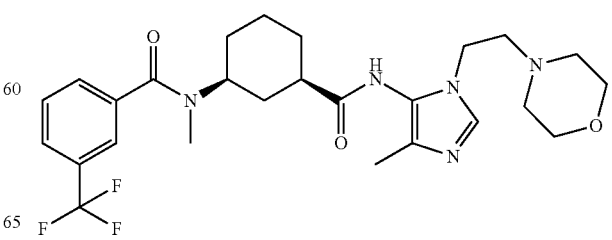

To a solution of cis-(chiral)-3-[methyl-[3-(trifluoromethyl)benzoyl]amino]cyclohexane carboxylic acid, Isomer 1 (0.2 g, 0.579 mmol) in pyridine (5 mL) is added 1-(3-dimethylaminopropyl)-3-ethylcarbodiimide hydrochloride (0.2718 g, 1.39 mmol) and 5-methyl-3-(2-morpholinoethyl)imidazol-4-amine (0.18 g, 0.87 mmol) under $N_2$ and the mixture is stirred at room temperature for 4 days. The mixture is concentrated in vacuo and the residue is purified by silica gel flash chromatography eluting with 10:1:0.1 dichloromethane:methanol $NH_3.H_2O$ followed by purification with preparative silica gel thin layer chromatography eluting with 10:1:0.1 dichloromethane:methanol:$NH_3.H_2O$ to give the title compound (0.04 g, 13.24%) as a white solid. LC/MS (m/z): 522 (M+H).

Example 19

Cis-(chiral)-N-[3-[(3,5-Dimethylimidazol-4-yl)carbamoyl]cyclohexyl]-N-methyl-3-(trifluoromethoxy)benzamide, Isomer 1

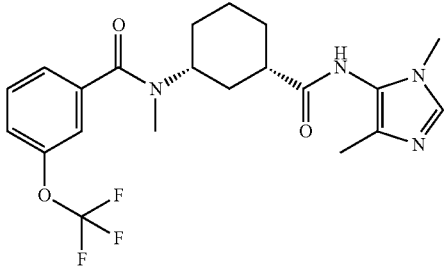 [SMILES: Cc1ncn(C)c1NC(=O)[C@H]1CCC[C@@H](N(C)C(=O)c2cccc(OC(F)(F)F)c2)C1]

1-(3-Dimethylaminopropyl)-3-ethylcarbodiimide hydrochloride (888 mg, 4.6 mmol) is added to a solution of cis-(chiral)-3-[methyl-[3-(trifluoromethoxy)benzoyl]amino]cyclohexanecarboxylic acid, Isomer 1 (640 mg, 1.9 mmol) and 3,5-dimethylimidazol-4-amine hydrochloride (410 mg, 2.8 mmol) in pyridine (20 mL) at room temperature and warmed to 58° C. The mixture is concentrated and the residue is purified with silica gel flash chromatography eluting with 20:1 dichloromethane:methanol and further purified with HPLC to give the title compound (253 mg, 31%). LC/MS (m/z): 439 (M+H).

Biological Assays

GPR142 Agonist Effect as Measured by IP-1 Assay

The purpose of this assay is to detect GPR142 agonist effect.

HEK293 cells expressing human GPR142 or mouse GPR142 are maintained in Dulbecco's modified Eagle's medium supplemented with 10% FBS and 800 μg/ml G418 (Geneticin®) at 37° C. and 5% $CO_2$. The cells are plated in 384 well plates at 5000 cells per well and allowed 18 hours for attachment. After addition of compounds at varying concentrations ranging from 30 μM to 1 nM, cells are incubated for 1 hour. IP-1 measurements are performed using an IP-One HTRF® assay kit (Cisbio) according to manufacturer's protocol using assay buffer containing 1×HBSS (+Ca, +Mg), 0.1% BSA, 50 mM LiCl and 20 mM HEPES, pH 7.2. The reaction is stopped by addition of IP1-d2 (IP-1 coupled to an organic HTRF acceptor) followed by cryptate solution (http://www.htrf.com/usa/htrf-chemistry) and the plates are incubated at 25° C. for 1 hour. Fluorescence is read in an Envision instrument at 665 nm and 620 nm wavelength. The ratio of 665 nm/620 nm is calculated and converted to IP-1 levels using an IP-1 standard curve. The data is fit to a 4 parameter-fit logistics to determine $EC_{50}$ values. All exemplified compounds exhibited an $EC_{50}$<150 nM using an assay substantially as described herein above.

Example 1 is tested as described above and exhibits an in vitro $EC_{50}$ of 52.6 nM (±27.5, n=9) and 105% efficacy (±11.6, n=9) against human GPR142 receptor and an $EC_{50}$ of 5.46 nM (±1.22, n=5) against mouse GPR142 receptor, (Mean±SEM; SEM=standard error of the mean.)

Glucose-dependent Insulin Secretion (GDIS) Assay

GDIS assays using primary murine pancreatic islets of Langerhans are used to characterize compounds. Pancreatic islets are isolated from male C57BL/6 mice by collagenase digestion and Dextran density gradient separation. The islets are cultured overnight in RPMI-1640 medium containing 11 mM glucose, 10% FBS, 2 mM glutamine. Insulin secretion is determined by a 60-minute incubation in KRB buffer (NaCl 7 g/L, KCl 0.35 g/L, $CaCl_2$ 0.28 g/L, $MgCl_2.7H_2O$ 0.24 g/L, $KH_2PO_4$ 0.16 g/L, $NaHCO_3$ 2.1 g/L and HEPES 2.38 g/L, pH=7.4, store at 4° C.) containing 0.1% BSA and appropriate glucose concentration (2.8 mM or 11.1 mM) in 48-well plates. Briefly, islets are preincubated in KRB buffer with 2.8 mM glucose and 0.5% BSA for 45 min They are then transferred to a 48-well plate (four islets/well) containing 300 μl/well of compound solutions prepared in 2.8 mM or 11.1 mM glucose and 0.1% BSA, and incubated at 37° C. and 5% $CO_2$ for 60 minutes. Incubation is stopped by refrigerating the plates at 4° C. for 3 minutes. Supernatant is removed from the wells and assayed for insulin levels using the Rat/Mouse Insulin Elisa kit (Millipore) or MA6000 Mouse/Rat Insulin Kit (MSD). Insulin secretion activity is normalized against control treatment (DMSO-1%) at 11 mM glucose. Active compounds have insulin secretion activity >1 fold (P<0.05) greater than DMSO control in the GDIS assay. For Example 1, it is significant to GDIS at 10 μM for p<0.05 and is not significant at 1 μM.

Example 1 is tested as described above and exhibits glucose dependent insulin secretion in a dose dependent manner in mouse islets.

Intraperitoneal Glucose Tolerance Tests (IPGTT)

IPGTT assay is used to examine the ability of exemplified compounds to activate GPR142 in vivo resulting in antidiabetic efficacy, i.e. reduction in plasma glucose levels. Male C57BL/6 mice (8-10 weeks of age) are fed normal rodent chow diet and water ad libitum. On the night before the study, animals are fasted overnight in clean cages. On the morning of the study, animals are dosed orally with vehicle or compound at the indicated doses 30 minutes prior to the glucose challenge (2 g/kg) by intraperitoneal injection. Blood glucose levels are determined from tail bleeds taken immediately prior to compound dosing (−30 min) and 0, 15, 30, and 60 min after glucose challenge using handheld glucometers. Plasma is isolated from tail bleeds taken at 7 minutes after glucose challenge and used to determine insulin levels by the Rat/Mouse Insulin Elisa kit (Millipore) or MA6000 Mouse/Rat Insulin Kit (MSD). The blood glucose profile from t=0 to t=60 min is used to calculate an area under the curve (AUC) for each treatment. Percent lowering in glucose AUC is calculated for each treatment group with respect to the AUC of vehicle group. Compounds with a reduction in glucose AUC (P<0.05) is considered positive in the assay.

Example 1 is tested as described above and exhibits glucose dependent insulin secretion and glucose lowering in a dose dependent manner in an IPGTT assay compared to the control, N-[(3-methylimidazol-4-yl)methyl]-1-[5-methyl-4-(2-thienyl)pyrimidin-2-yl]-5-propyl-pyrazole-4-carboxamide as shown in Table 1 below with an $ED_{50}$ of 4.2 mpk and an $ED_{80}$ of 9.1 mpk in lean C57BL/6 mice.

TABLE 1

| IPGTT in Normal C57BL/6Mice | | |
|---|---|---|
| Example | Glucose AUC suppression at 30 mg/kg compared to vehicle control (%) | Increase of glucose-stimulated insulin release at 30 mg/kg compared to vehicle control (%) |
| 1 | 43 | 200 |

We claim:

1. A compound of the Formula

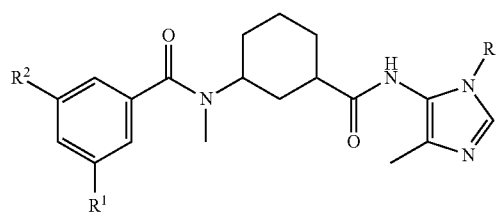

wherein R is selected from the group consisting of $CH_3$, $CH(CH_3)_2$, $CH_2CN$, $CH_2CHF_2$, $CH_2CF_3$,

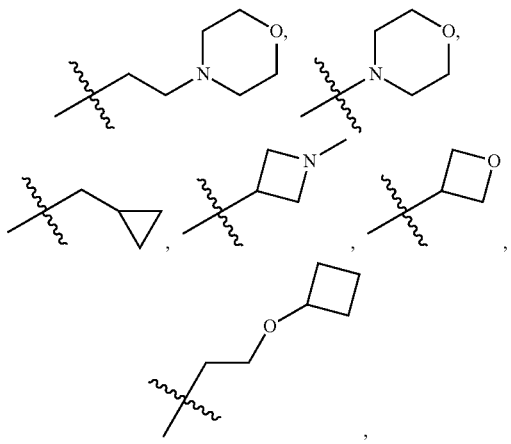

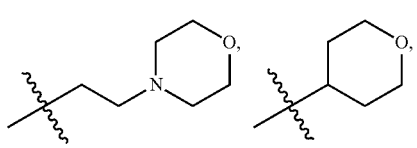

$CH_2CH_2OCH_3$, and $CH_2C(O)OCH(CH_3)_2$, $R^1$ is selected from the group consisting of $CF_3$, $OCF_3$, and Cl;

$R^2$ is selected from the group consisting of H and F;

or a pharmaceutically acceptable salt thereof.

2. A compound, or pharmaceutically acceptable salt thereof, as claimed by claim 1, wherein R is selected from the group consisting of $CH(CH_3)_2$, $CH_2CN$, $CH_2CHF_2$, $CH_2CF_3$,

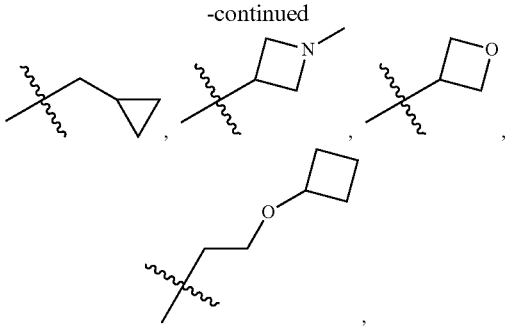

$CH_2CH_2OCH_3$, and $CH_2C(O)OCH(CH_3)_2$.

3. A compound, or pharmaceutically acceptable salt thereof, as claimed by claim 1, wherein $R^2$ is H.

4. A compound, or pharmaceutically acceptable salt thereof, as claimed by claim 1 wherein $R^1$ is selected from the group consisting of $CF_3$ and $OCF_3$.

5. A compound, or pharmaceutically acceptable salt thereof, as claimed by claim 4 wherein $R^1$ is $CF_3$.

6. A compound, or pharmaceutically acceptable salt thereof, as claimed by claim 1 wherein R is selected from the group consisting of

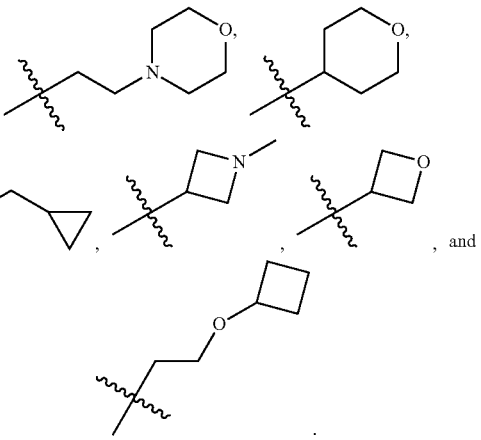

, and

7. A compound, or pharmaceutically acceptable salt thereof, as claimed by claim 1, wherein R is selected from the group consisting of $CH_3$, $CH(CH_3)_2$, $CH_2CN$, $CH_2CHF_2$, $CH_2CF_3$, $CH_2CH_2OCH_3$, and $CH_2C(O)OCH(CH_3)_2$.

8. A compound of the Formula

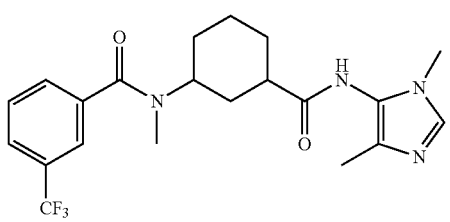 [SMILES: Cc1ncn(C)c1NC(=O)C1CCCC(N(C)C(=O)c2cccc(C(F)(F)F)c2)C1]

or a pharmaceutically acceptable salt thereof.

9. A compound or salt as claimed by claim 1 wherein the compound is Cis-(chiral)-N-[3-[(3,5-Dimethylimidazol-4-yl)carbamoyl]cyclohexyl]-N-methyl-3-(trifluoromethyl)benzamide.

10. A pharmaceutical composition comprising a compound as claimed by claim 1, or a pharmaceutically acceptable salt thereof, and at least one of a pharmaceutically acceptable carrier, diluent, or excipient.

11. A method for treating type II diabetes in a mammal in need thereof, comprising administering to the mammal an effective amount of a compound, or a pharmaceutically acceptable salt thereof, as claimed by claim 1.

12. A method for treating type II diabetes in a mammal in need thereof, comprising administering to the mammal an effective amount of a compound, or a pharmaceutically acceptable salt thereof, as claimed by claim 9.

13. A pharmaceutical composition comprising a compound as claimed by claim 9, or a pharmaceutically acceptable salt thereof, and at least one of a pharmaceutically acceptable carrier, diluent, or excipient.

\* \* \* \* \*

UNITED STATES PATENT AND TRADEMARK OFFICE
CERTIFICATE OF CORRECTION

PATENT NO. : 9,861,613 B2
APPLICATION NO. : 15/116230
DATED : January 9, 2018
INVENTOR(S) : Zhi Long Hu et al.

Page 1 of 1

It is certified that error appears in the above-identified patent and that said Letters Patent is hereby corrected as shown below:

In the Specification

In Column 2, Line 14, After "  " insert -- (F) --.

In the Claims

In Column 37, Line 31, In Claim 1, delete "CH$_2$CHF$_2$,CH$_2$CF$_3$," and insert -- CH$_2$CHF$_2$, CH$_2$CF$_3$, --, therefor.

In Column 37, Line 32-36, In Claim 1, delete "  " and insert -- --, therefor.

In Column 37, Line 51, In Claim 1, delete "CH$_2$C(O)OCH(CH$_3$)$_2$," and insert -- CH$_2$C(O)OCH(CH$_3$)$_2$; --, therefor.

In Column 38, Line 49, In Claim 7, delete "CH$_2$CH$_2$OCH$_3$,and" and insert -- CH$_2$CH$_2$OCH$_3$, and --, therefor.

Signed and Sealed this
Seventeenth Day of April, 2018

Andrei Iancu
*Director of the United States Patent and Trademark Office*